(12) United States Patent
Roumeas et al.

(10) Patent No.: US 10,030,009 B2
(45) Date of Patent: Jul. 24, 2018

(54) FLAVONOID DERIVATIVE COMPOUNDS AND METHOD FOR PREPARING SAME BY DEPOLYMERIZATION OF CONDENSED TANNINS

(71) Applicants: INSTITUT NATIONAL DE LA RECHERCHE AGRONOMIQUE, Paris (FR); CENTRE INTERNATIONAL D'ETUDES SUPERIEURES EN SCIENCES AGRONOMIQUES, Montpellier (FR); UNIVERSITE DE MONTPELLIER 1, Montpellier (FR)

(72) Inventors: Laurent Roumeas, Montpellier (FR); Hélène Fulcrand, Saint Gely du Fesc (FR); Chahinez Aouf, Montpellier (FR); Eric Dubreucq, Montpellier (FR)

(73) Assignees: INSTITUT NATIONAL DE LA RECHERCHE AGRONOMIQUE, Paris (FR); CENTRE INTERNATIONAL D'ETUDES SUPERIEURES EN SCIENCES AGRONOMIQUES, Montpellier (FR); UNIVERSITE DE MONTPELLIER 1, Montpellier (FR)

(*) Notice: Subject to any disclaimer, the term of this patent is extended or adjusted under 35 U.S.C. 154(b) by 3 days.

(21) Appl. No.: 15/329,991

(22) PCT Filed: Aug. 3, 2015

(86) PCT No.: PCT/FR2015/052144
§ 371 (c)(1),
(2) Date: Jan. 27, 2017

(87) PCT Pub. No.: WO2016/020615
PCT Pub. Date: Feb. 11, 2016

(65) Prior Publication Data
US 2017/0260170 A1    Sep. 14, 2017

(30) Foreign Application Priority Data
Aug. 4, 2014    (FR) ...................................... 1457584

(51) Int. Cl.
C07D 407/04    (2006.01)
(52) U.S. Cl.
CPC .................. C07D 407/04 (2013.01)
(58) Field of Classification Search
CPC .................................................. C07D 407/04
See application file for complete search history.

(56) References Cited

U.S. PATENT DOCUMENTS

| 2,776,981 A | 1/1957 | Tyran |
| 7,064,222 B2 | 6/2006 | Ahmed |
| 8,088,419 B2 | 1/2012 | Nonaka et al. |

OTHER PUBLICATIONS

Deodhar, M., "Synthesis of oxygenated 4-arylisoflavans and 4-arylflavans." Tetrahedron Letters 53.49 (2012): 6697-6700.*
Chen et al., "One-pot depolymerizative extraction of proanthocyanidins from mangosteen pericarps," Food Chemistry, Jun. 1, 2009, pp. 874-880, vol. 114, No. 3, Elsevier Ltd, NL.
Roumeas et al., "Depolymerisation of condensed tannins in ethanol as a gateway to biosourced phenolic synthons," Green Chemistry, Jan. 1, 2013, pp. 3268-3275, vol. 15, No. 11.
Selga et al., Efficient one pot extraction and depolymerization of grape (*Vitis vinifera*) Pomace Procyanidins for the Preparation of Antioxidant Thio-Conjugates, Journal of Agricultural and Food Chemistry, Feb. 1, 2004, pp. 167-473, vol. 52, No. 3.

* cited by examiner

*Primary Examiner* — John Matthew Mauro
(74) *Attorney, Agent, or Firm* — Im IP Law; C. Andrews Im

(57) ABSTRACT

A compound of general formula (I) in which $R_1$, $R_2$, $R_3$ and $R_5$, identical or different, each represent a hydrogen atom or a hydroxyl group, optionally protected by a protecting group. $R_4$ represents a hydrogen atom or an —$OR_7$ group, in which $R_7$ represents a hydrogen atom, a protecting group or a gallate group. $R_6$ represents a hydroxyl group, optionally protected by a protecting group. $R'_1$, $R'_2$, $R'_3$ and $R'_4$, identical or different, each represent a hydrogen atom or a substituent not comprising a mesomeric electron withdrawing group conjugated with the furan ring. A substituent from $R'_1$, $R'_2$, $R'_3$ and $R'_4$ representing the covalent bond with the pyran ring or one of the salts of same. A method for obtaining such a compound includes a step of depolymerization of condensed tannins in the presence of an acid by means of a nucleophile derived from furan.

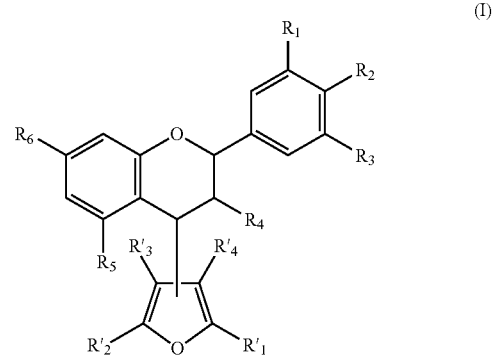

21 Claims, 3 Drawing Sheets

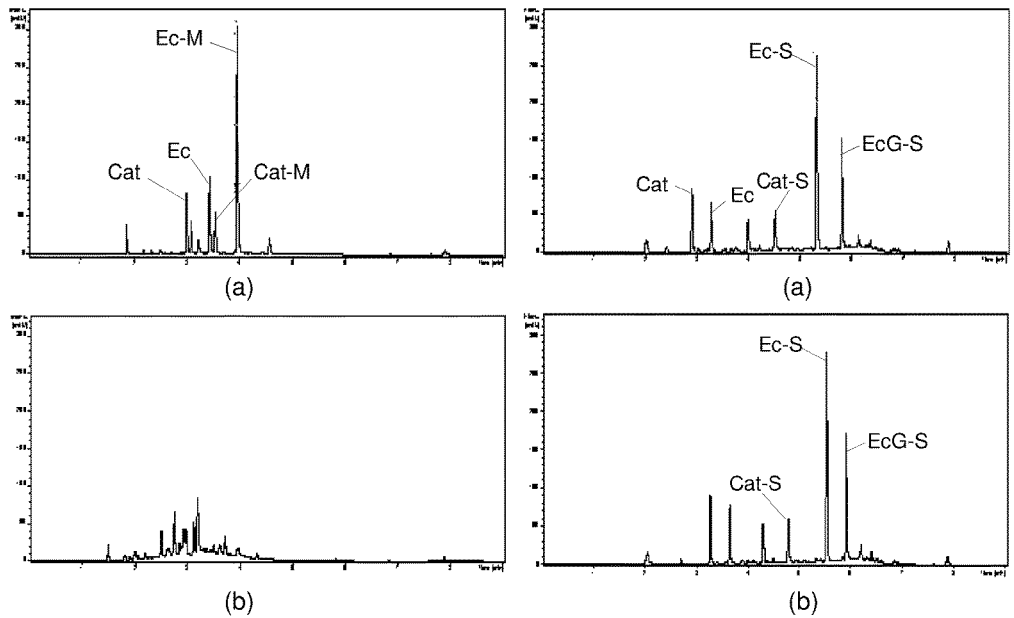
FIG 6                                    FIG 7
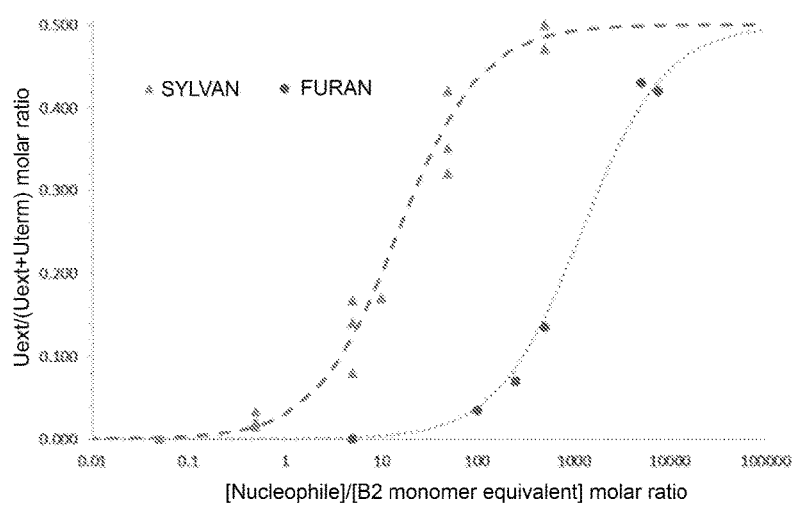
FIG 8

FLAVONOID DERIVATIVE COMPOUNDS AND METHOD FOR PREPARING SAME BY DEPOLYMERIZATION OF CONDENSED TANNINS

RELATED APPLICATIONS

This application is a § 371 application from PCT/FR2015/052144 filed Aug. 3, 2015, which claims priority from French Patent Application No. 14 57584 filed Aug. 4, 2014, each of which is incorporated herein by reference in its entirety.

FIELD OF THE INVENTION

The present invention relates to a flavonoid-derived aromatic compound, to a process for obtaining such a compound, by depolymerization of polyfunctional polyaromatic compounds derived from renewable resources, more particularly of condensed tannins, and also to the use of furan-derived compounds for the depolymerization of condensed tannins.

BACKGROUND OF THE INVENTION

In order to solve the problem of being dependent on fossil energies, and to reduce the pollution associated with the implementation of chemical reactions, it proves to be of increasing interest to develop processes for producing chemical compounds of interest from renewable natural resources, which are environmentally friendly. Thus, the obtaining of synthons, in particular of phenolic synthons, derived from biomass, as platform molecules for the chemical industry, has become an important challenge for this industry.

In particular, numerous studies have been carried out for a few years in order to take advantage of the advantageous properties of natural compounds, such as plant polyphenols, which are capable of constituting substitutes for phenolic petrochemical compounds, such as bisphenol A. Among them, condensed tannins, also known as proanthocyanidins, are the most abundant in plants, in particular terrestrial plants, after lignin. These compounds are found in particular in numerous varied available natural resources such as food-processing residues, for example in fruit marcs, and unexploited biomass, in particular in the bark, leaves and needles of trees, grapevine, fruit, etc.

Condensed tannins are oligomers or polymers of polyfunctional polyaromatic monomers. These monomers belong to the class of flavan-3-ols, of general formula:

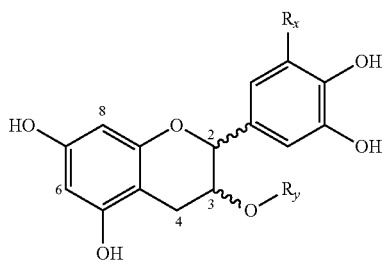

wherein $R_x$ represents a hydrogen atom or a hydroxyl group, and $R_y$ represents a hydrogen atom or a gallate group of formula:

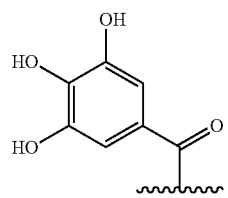 [SMILES: *C(=O)c1cc(O)c(O)c(O)c1]

Through depolymerization of condensed tannins, (+)catechin and (−)epicatechin monomers, and also derivatives substituted mainly at C4 and potentially at C2, are in particular obtained. The C2, C3 and C4 carbon atoms of these derivatives are asymmetrical, and stereoisomers other than those initially present in the structures of tannins can also be formed during the depolymerization reaction. The aromatic nature of these monomers combined with the presence of free hydroxyl functions gives them properties which make them preferred candidates for constituting starting reagents for the industrial synthesis of active products, for numerous and varied applications.

Thus, various processes for depolymerizing condensed tannins, aimed at obtaining therefrom the constituent monomers, termed terminal units, and/or derived monomers, termed extension units, have been proposed by the prior art, essentially for analytical purposes.

It has in particular been shown that condensed tannins can be depolymerized in an acidic medium by means of sulfur-bearing nucleophiles. Such a prior art can for example be illustrated by the various publications by Chen et al., 2009; U.S. Pat. No. 8 088 419; Roumeas et al., 2013; and Selga et al., 2004, which describe the depolymerization of biobased condensed tannins by thiolysis. Such an "analytical" depolymerization process makes it possible to obtain, with a high yield, flavonoid derivatives that are of use for a wide range of applications, for example of general formula:

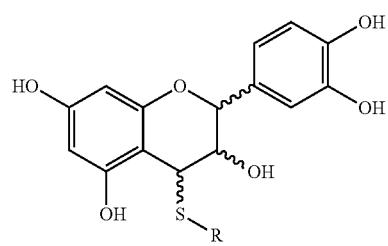

in which R represents $(CH_2)_2$—OH, $CH_2$—COOMe, $(CH_2)_2$—$NH_2$ or $CH_2$—$CH(NH_2)$—COOH.

However, the derivatives of this type are unstable under alkaline conditions, that is to say typically at a pH above 8.5, in which conditions the sulfur-bearing group becomes nucleofugal. Thus, it has been noted by the present inventors that, at a pH equal to 9, the derivatives derived from a depolymerization carried out by means of 2-mercaptoethanol as nucleophile are more than 95% degraded after 19 h at ambient temperature. Advantage has in particular been taken of this property in order to create novel derivatives resulting from tannin depolymerization by thiolysis (Chen et al., 2009).

However, it has been noted by the present inventors that the instability of the sulfur-bearing depolymerization derivatives under alkaline conditions is prejudicial to the implementation of certain subsequent reactions for functionalizing the hydroxyl groups of the phenolic nuclei, which are necessary for certain applications.

OBJECT AND SUMMARY OF THE INVENTION

An objective of the present invention is thus to provide flavonoid-derived compounds which have a stability in basic medium which is greater than that of the compounds proposed by the prior art, so as to broaden the field of application of such compounds, and in particular the type of functionalization reactions to which these compounds can be subjected in order to form products of interest for a wide range of applications.

An additional objective of the invention is to provide a method for obtaining such compounds from biobased substances.

The present invention in particular also aims for such a method to be environmentally friendly, for it to be simple and inexpensive to carry out, and for it to make it possible to obtain the compounds according to the invention rapidly and with a high yield.

Thus, the present invention provides a flavonoid-derived compound, termed furan-flavan monomer, in which a flavonoid residue is bonded, by covalent bonding, at the level of the pyran ring, to a furan derivative, of general formula (I):

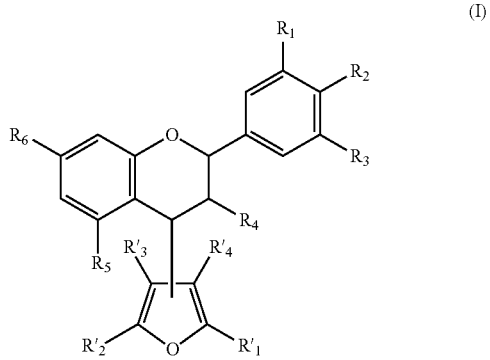

in which:

$R_1$, $R_2$, $R_3$ and $R_5$, which may be identical or different, each represent a hydrogen atom or a hydroxyl group, optionally protected by a hydroxyl-function-protecting group, $R_4$ represents a hydrogen atom or an —$OR_7$ group, in which $R_7$ represents a hydrogen atom, a hydroxyl-function-protecting group or a group of general formula (II):

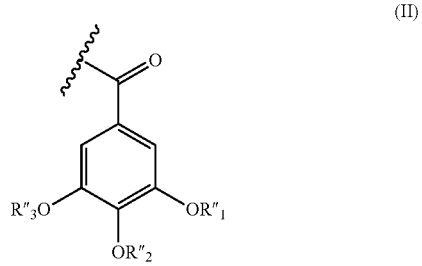

in which $R''_1$, $R''_2$ and $R''_3$, which may be identical or different, each represent a hydrogen atom or a hydroxyl-function-protecting group, $R_6$ represents a hydroxyl group, optionally protected by a hydroxyl-function-protecting group, and $R'_1$, $R'_2$, $R'_3$ and $R'_4$, which may be identical or different, each represent a hydrogen atom or a substituent not comprising a mesomeric-effect electron-withdrawing group conjugated to the furan nucleus, one substituent among $R'_1$, $R'_2$, $R'_3$ and $R'_4$ representing the covalent bond with the pyran ring of the flavonoid residue, illustrated by the variable attachment bond in general formula (I), or a salt thereof.

The term "hydroxyl-function-protecting group" is intended to mean any group used conventionally in itself for protecting a hydroxyl function, more particularly a phenolic hydroxyl, that is to say for masking its reactivity with a view to subsequent reactions. Each of the hydroxyl-function-protecting groups can for example be chosen from groups alkyl, acyl, in particular acetyl, benzyl, silyl, sulfonyl, etc., groups. The hydroxyl-function-protecting groups borne by the compound according to the invention may all be identical, or may be different from one another, the protecting groups borne by the hydroxyl functions of one and the same nucleus then preferably being identical to one another.

General formula (I) encompasses all the possible combinations of isomeric forms at the level of the asymmetric carbons, and all the mixtures of such isomeric forms. Each particular isomer can be obtained from a mixture of isomers by purification methods which are conventional in themselves for those skilled in the art.

The term "substituent not comprising a mesomeric-effect electron-withdrawing group conjugated to the furan nucleus" is intended to mean any substituent comprising no mesomeric-effect electron-withdrawing group which is bonded directly, or by conjugation, to the furan ring of the compound of general formula (I). It is within the competence of those skilled in the art to determine, on the basis of their general knowledge, which substituents do or do not fall under such a definition. The general knowledge of those skilled in the art in this subject is in particular illustrated by the handbook by René Milcent, Chimie organique: Stéréochimie, entités réactives et réactions [Organic chemistry: Stereochemistry; reactive entities and reactions], EDP Sciences—2007, in particular in chapters 5.5 and 5.6.

By way of example, substituents excluded from the definition of $R'_1$, $R'_2$, $R'_3$ and $R'_4$, are substituents comprising, bonded directly or by conjugation to the furan ring, an electron-withdrawing radical such as a nitro, carbonyl, carboxylic or sulfonic radical, optionally salified or esterified, or an amide, cyano, sulfonyl, etc., radical.

The compound according to the invention may in particular be such that, in general formula (I), $R'_1$, $R'_2$, $R'_3$ and $R'_4$, which may be identical or different, each represent, with the exception of the substituent forming the covalent bond with the pyran ring:

a hydrogen atom,
 a halogen atom, such as a fluorine, chlorine, bromine or iodine atom,
  a group comprising an inductive-effect or mesomeric-effect electron-donating radical, bonded directly or by conjugation to the furan ring, for example chosen from an amino, oxy or thio radical, which is optionally substituted, said group not comprising any mesomeric-effect electron-withdrawing group conjugated to the furan nucleus, or
 a linear, branched and/or cyclic carbon-based radical, possibly comprising a single ring or several condensed rings, which is saturated and/or unsaturated, optionally aromatic, which is optionally substituted, optionally comprising one or more heteroatoms and/or one or more groups comprising one or more heteroatoms, each heteroatom being in particular chosen from O, N, P, Si and S, said carbon-based radical not comprising any mesomeric-effect electron-withdrawing group conjugated to the furan nucleus.

Preferentially, in general formula (I), at least one substituent among $R'_1$, $R'_2$, $R'_3$ and $R'_4$ represents a hydrogen atom.

The covalent bond $R'_1$, $R'_2$, $R'_3$ or $R'_4$, linking the flavonoid residue and the furan derivative in the compound of general formula (I) according to the invention, is in particular stable in a basic medium, and it is not prone to allowing a repolymerization or a degradation in such a medium, contrary to the bonds of the derivatives obtained by depolymerization of condensed tannins using sulfur-bearing compounds proposed by the prior art. It has in particular been demonstrated by the present inventors that the compound of general formula (I) according to the invention remains stable and unchanged both in an aqueous solution at pH 9 and ambient temperature, and in an organic medium containing a base. The compound according to the invention can thus advantageously be used directly in a basic medium for the preparation of active products involving a phenol functionalization which comprises a deprotonation step.

The compound according to the invention can thus be easily functionalized, both under acidic conditions and neutral or alkaline conditions, with a view to the preparation of active products advantageously taking advantage of the properties associated with the presence in its structure not only of a backbone of flavanoid type, with a benzopyran structure, but also of a furan nucleus. In particular, substituents comprising electron-withdrawing groups such as, for example, those excluded for the furan nucleus of the compound of general formula (I), may be introduced in order to confer additional functionalities on this compound.

Thus, the properties of the phenolic nuclei, combined with the overall physicochemical properties of the compound ensuing from its structure, confer on the latter multiple properties, in particular antioxidant, antimicrobial, photochemical and sensory properties, which, combined with its chemical reactivity, make it entirely advantageous for a large number of applications.

The compound according to the invention thus has an application in numerous fields, in particular, but not in a limiting manner, in fields such as the materials field, the cosmetics field, the food-processing field, the medical field, the photovoltaic field, or the polymer field, for example for surface treatment.

The compound according to the invention may in particular consist of a catechin derivative, of general formula (Ia):

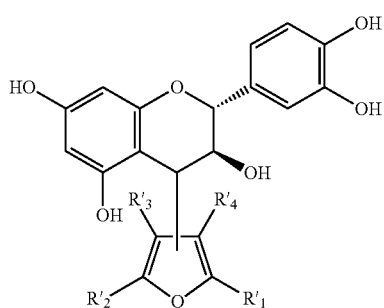

or of an epicatechin derivative, of general formula (Ib):

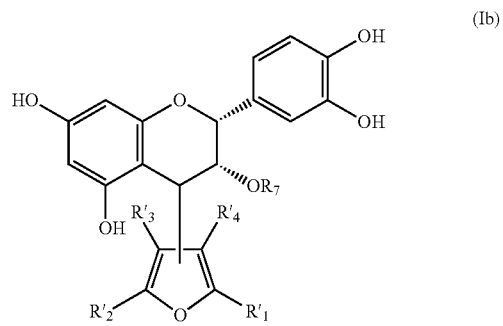

in which formulae $R'_1$, $R'_2$, $R'_3$ and $R'_4$, and $R_7$, are as described above and below with reference to general formula (I).

The compound according to the invention may in particular be such that, in general formula (I), $R'_1$, $R'_2$, $R'_3$ and $R'_4$, which may be identical or different, each represent, when they do not form the covalent bond with the flavonoid residue, a hydrogen atom or a linear or branched hydrocarbon-based radical which is optionally substituted and which is optionally interrupted with one or more heteroatoms and/or with one or more groups comprising one or more heteroatoms, each heteroatom possibly being, for example, chosen from O, N, P, Si and S, said hydrocarbon-based radical not comprising any mesomeric-effect electron-withdrawing group conjugated to the furan nucleus.

Compounds according to the invention may in particular correspond to general formulae (Ic) and (Id) below:

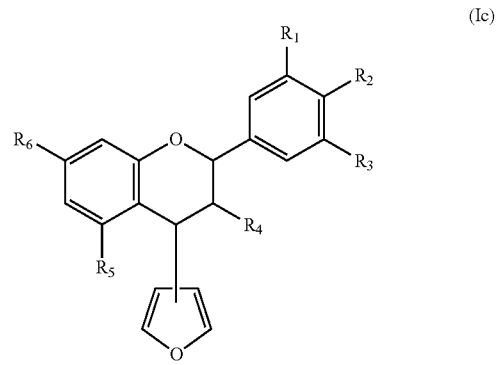

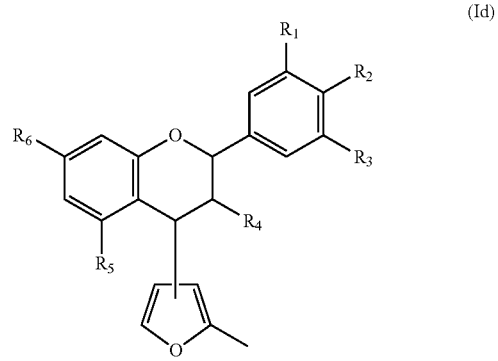

in which formulae $R_1$, $R_2$, $R_3$, $R_4$, $R_5$ and $R_6$ are as described above with reference to general formula (I).

In variants of the invention, in general formula (I) below, $R'_1$, $R'_2$, $R'_3$ and $R'_4$ correspond in particular to one or more of the characteristics below, taken alone or in each of their possible combinations:

$R'_1$ represents the covalent bond with the pyran ring,
$R'_3$ and $R'_4$ each represent a hydrogen atom,
$R'_2$ represents a hydrogen atom or $R'_2$ represents an alkyl group, in particular with a linear chain, which is preferably $C_1$-$C_{18}$, more preferably $C_1$-$C_{10}$, and preferentially $C_1$-$C_4$. In particular, $R'_2$ may represent a methyl radical.

In particular, in general formula (I), all three of $R'_2$, $R'_3$ and $R'_4$ may represent a hydrogen atom, and $R'_1$ may represent the covalent bond with the pyran ring, the compound according to the invention then corresponding to general formula (Ie):

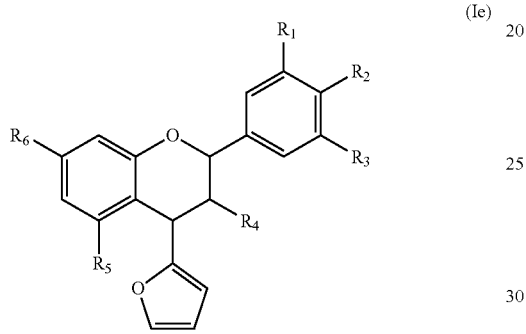

(Ie)

in which $R_1$, $R_2$, $R_3$, $R_4$, $R_5$ and $R_6$ are as defined above with reference to general formula (I).

In the present description the expression "furylated extension unit" will be used to denote such a compound.

In variants of the invention, $R_1$, $R_2$, $R_3$, $R_4$, $R_5$ and $R_6$, and $R'_1$, $R'_2$, $R'_3$ and $R'_4$, are as defined above with reference to general formula (I), at least one group among $R'_1$, $R'_2$, $R'_3$ and $R'_4$ representing, however, neither a hydrogen atom nor the covalent bond with the pyran ring.

The compound according to the invention may in particular be such that, in general formula (I), $R'_3$ and $R'_4$ each represent a hydrogen atom, $R'_1$ represents the covalent bond with the pyran ring, and $R'_2$ represents an alkyl group, in particular with a linear chain, which is preferably $C_1$-$C_{18}$, more preferably $C_1$-$C_{10}$, and preferentially $C_1$-$C_4$. In particular, $R'_2$ then represents a methyl radical, the compound then corresponding to general formula (If) below, in which $R_1$, $R_2$, $R_3$, $R_4$, $R_5$ and $R_6$ are as defined above:

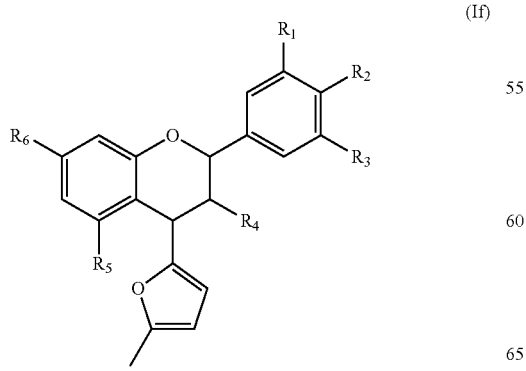

(If)

In the present description, the expression "sylvanylated extension unit" will be used to denote such a compound.

A compound corresponding to such a general formula (If) is especially particularly compatible with use in the food field.

In other variants of the invention, in general formula (I), $R'_1$ and $R'_2$ represent neither a hydrogen atom nor the covalent bond with the pyran ring, $R'_3$ represents a hydrogen atom and $R'_4$ represents the covalent bond with the pyran ring. $R'_1$ and $R'_2$ may for example each represent a methyl group, the compound according to the invention then corresponding to general formula (Ig):

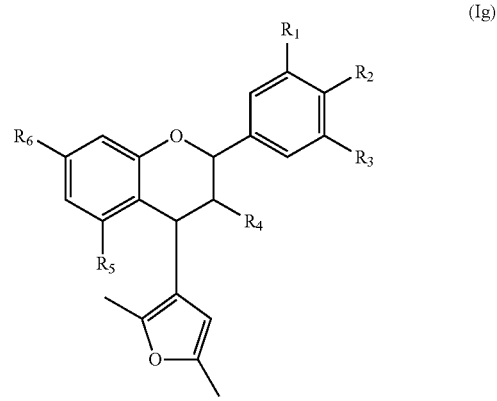

(Ig)

Particular compounds according to the present invention correspond respectively to the formulae below:

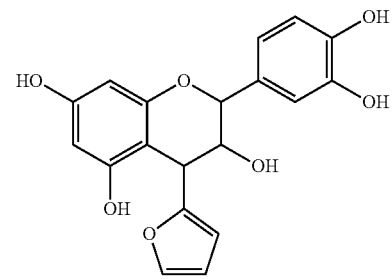

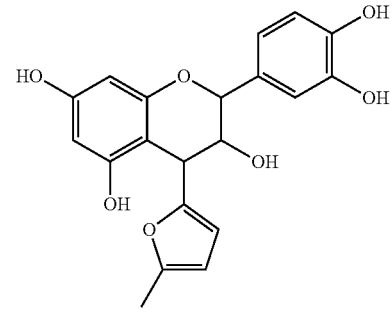

Another aspect of the invention relates to a method for obtaining a compound according to the invention of general formula (I), as defined above. This method comprises a depolymerization step of depolymerizing condensed tannins in the presence of an acid by means of a nucleophile, termed furan derivative, of general formula (III):

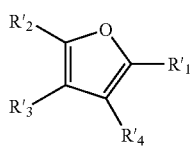

(III)

in which R'$_1$, R'$_2$, R'$_3$ and R'$_4$, which may be identical or different, each represent a hydrogen atom or a substituent not comprising any mesomeric-effect electron-withdrawing group conjugated to the furan nucleus. At least one substituent among R'$_1$, R'$_2$, R'$_3$ and R'$_4$ represents a hydrogen atom, so as to allow the formation of the covalent bond with the pyran ring of the flavonoid residue of a condensed tannin extension unit, leading to the obtaining of a compound of general formula (I) according to the invention.

In particular, in general formula (III), R'$_1$, R'$_2$, R'$_3$ and R'$_4$ may correspond to one of the characteristics below, or to any combination of several of these technically compatible characteristics:

R'$_1$, R'$_2$, R'$_3$ and R'$_4$, which may be identical or different, each represent:
  a hydrogen atom,
  a halogen atom, such as a fluorine, chlorine, bromine or iodine atom,
  a group comprising an electron-donating radical bonded directly or by conjugation to the furan ring, for example chosen from an amino, oxy or thio radical, which is optionally substituted, or
  a linear, branched and/or cyclic carbon-based radical, possibly comprising a single ring or several condensed rings, which is saturated and/or unsaturated, optionally aromatic, which is optionally substituted, optionally comprising one or more heteroatoms and/or one or more groups comprising one or more heteroatoms;

at least two substituents among R'$_1$, R'$_2$, R'$_3$ and R'$_4$ represent a hydrogen atom;

R'$_1$, R'$_2$, R'$_3$ and R'$_4$, which may be identical or different, each represent a hydrogen atom or a linear or branched, optionally substituted, hydrocarbon-based radical which is optionally interrupted with one or more heteroatoms and/or with one or more groups comprising one or more heteroatoms, said hydrocarbon-based radical not comprising any mesomeric-effect electron-withdrawing group conjugated to the furan nucleus;

R'$_1$, R'$_3$ and R'$_4$ each represent a hydrogen atom;

R'$_2$ represents an alkyl group, in particular with a linear chain, which is preferably C$_1$-C$_{18}$, more preferably C$_1$-C$_{10}$, and preferentially C$_1$-C$_4$; R'$_2$ representing for example a methyl radical;

R'$_2$ represents a hydrogen atom;

at least one group among R'$_1$, R'$_2$, R'$_3$ and R'$_4$ does not represent a hydrogen atom.

In particular, when, in general formula (III), at least one substituent among R'$_1$, R'$_2$, R'$_3$ and R'$_4$ represents a group comprising an electron-donating radical bonded directly or by conjugation to the furan ring, for example chosen from an amino, oxy or thio radical, which is optionally substituted, or a linear, branched and/or cyclic carbon-based radical, possibly comprising a single ring or several condensed rings, which is saturated and/or unsaturated, optionally aromatic, which is optionally substituted, optionally comprising one or more heteroatoms and/or one or more groups comprising one or more heteroatoms, the presence of such a substituent advantageously promotes the depolymerization reaction, in particular compared with the unsubstituted furan.

In particular embodiments of the invention, in general formula (III):
  R'$_1$ represents a hydrogen atom;
  R'$_2$ represents a hydrogen atom or an alkyl group, in particular with a linear chain, which is preferably C$_1$-C$_{18}$, more preferably C$_1$-C$_{10}$, and preferentially C$_1$-C$_4$, for example a methyl radical;
  R'$_3$ and R'$_4$ each represent a hydrogen atom.

Bringing together, in an acidic medium, condensed tannins and a nucleophile derived from furan of formula (III) above induces the release, on the one hand, of the condensed tannin extension units, and, on the other hand, of the terminal units in their native form, in particular of catechin/epicatechin units, of formula:

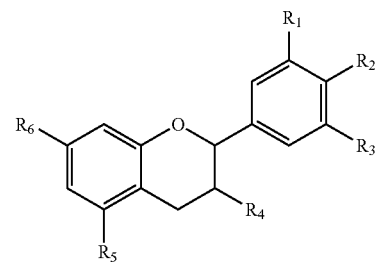

The nucleophile of general formula (III) reacts with the extension units thus released, so as to form, by furylation, a furan-flavan monomer of general formula (I), or a mixture of such monomers.

There will be no preconception here of the mechanism underlying the obtaining of the compounds of general formula (I) in accordance with the invention by means of such a depolymerization reaction. However, it may be assumed that the nucleophile of general formula (III) has particularly advantageous properties, which are taken advantage of during the reaction in order to stabilize the carbocations resulting from the cleavage of the interflavan bond, and to shift the equilibrium of the reaction toward the depolymerized forms, which are stable under alkaline conditions.

The method according to the invention is particularly simple to carry out, this being at low cost.

In order to meet one of the objectives set by the present invention, namely that this method is as environmentally friendly as possible, and allows the exploitation of local agro-resources, the method according to the invention is preferentially carried out using condensed tannins derived from renewable resources such as the by-products and coproducts of the agricultural or wine industry, for example fruit marcs, wood barks, etc., and unexploited biomasses, such as pine needles, dead leaves, etc.

The depolymerization step of the method according to the invention can be carried out using condensed tannins which have been previously isolated from biomass. The method then comprises a prior step of extracting the condensed tannins from biomass, for example from grape seeds. Such an extraction can be carried out by any technique known to those skilled in the art, in particular the techniques illustrated by the publications by Prieur et al., 1994, and Rigaud et al., 1993.

The depolymerization step can also be preceded by a step of protecting one or more of the hydroxyl functions borne by the tannins, with any hydroxyl-function-protecting group which is conventional in itself.

Alternatively, the depolymerization step can be carried out directly from biomass, without prior extraction of the condensed tannins contained in this biomass, for example directly on a bark fraction, such as a fraction of *Pseudotsuga menziesil* (Douglas pine) bark.

In preferred embodiments of the invention, the furan derivative of general formula (III), acting as a nucleophile for the condensed tannin depolymerization reaction, is also biobased.

Thus, the furanic nucleophiles may be derived from biomass, in particular from hydrogenated products of furaldehyde, the latter being derived from a process for dehydration of pentose (xylan), or else may be present in the form of furan groups in certain lipids as described, for example, by Liengprayoon et al., 2011.

In particular, in general formula (III) above, all four of R'$_1$, R'$_2$, R'$_3$ and R'$_4$ may represent a hydrogen atom. The nucleophile used for the condensed tannin depolymerization reaction is then the furan of general formula (IIIa):

(IIIa)

The furan can in particular be produced industrially from furfural (U.S. Pat. No. 2,776,981), the latter being itself of agricultural origin, and obtained by acid dehydration and distillation of plant pentoses (Adams et al., 1921).

Such a compound, and derivatives thereof, consequently fall particularly well within a process corresponding to the principles of sustainable green chemistry.

When the nucleophile is furan, the term "furanolysis" will denote, in the present description, the depolymerization method according to the invention. Such a reaction leads to the obtaining of compounds according to the invention corresponding to general formula (Ie) above.

In other particular embodiments of the invention, in general formula (III) above, R'$_1$, R'$_3$ and R'$_4$ each represent a hydrogen atom and R'$_2$ represents a methyl radical. The nucleophile used for the condensed tannin depolymerization reaction is then 2-methylfuran, also known as sylvan, of general formula (IIIb):

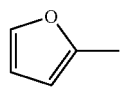

(IIIb)

Sylvan, like furan, constitutes an industrial and renewable carbon source derived from biomass. It can in particular be obtained by a treatment which hydrogenates the aldehyde of furfural, generally catalyzed by cupric and/or chromic catalysts (Burnett et al., 1948), its production also being the subject of the development of catalytic hydrogenation processes (U.S. Pat. No. 7,064,222) or electrochemical processes (Li et al., 2012).

Sylvan offers in particular the advantage of particularly good compatibility with use in the food sector. In addition, it proves to be more effective than furan for condensed tannin depolymerization, in particular in terms of reactivity.

When the nucleophile is sylvan, the term "sylvanolysis" will, in the present description, denote the depolymerization method according to the invention. Such a reaction leads to the obtaining of compounds according to the invention corresponding to general formula (If) above.

Generally, furan and sylvan also have the advantage of being easily recyclable by distillation, owing to their low boiling point which, at atmospheric pressure, is below 32° C. for furan, and below 66° C. for sylvan.

An example of another nucleophile which can be used for the condensed tannin depolymerization reaction is 2,5-dimethylfuran, of general formula (IIIc):

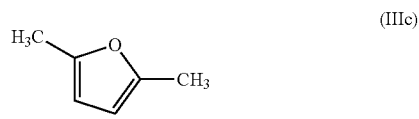

(IIIc)

in which R'$_1$ and R'$_2$ each represent a methyl radical, and R'$_3$ and R'$_4$ each represent a hydrogen atom.

Such a reaction leads to the obtaining of compounds according to the invention corresponding to general formula (Ig) above.

The exact optimal operating parameters of the method according to the invention depend on the particular structure of the nucleophile of general formula (III) used. It is within the competence of those skilled in the art to determine these parameters appropriately, for each particular nucleophile, on the basis of the more general preferential characteristics set out hereinafter, in order to obtain, with the fastest possible reaction rate, high reaction yields, in particular close to 100%, while limiting in particular the competitive reaction of reaction products degradation.

Generally, it has been observed by the present inventors that the depolymerization reaction requires an excess of nucleophile of general formula (III) relative to the tannins, owing to the intrinsic nucleophilic force of the latter and to their monomeric forms, which compete with the nucleophile reagent. This excess depends on the nature of the nucleophile involved.

In particular embodiments of the method according to the invention, for the depolymerization step, the "nucleophile of general formula (III)/depolymerizable condensed tannins" molar ratio is greater than or equal to the "nucleophile of general formula (III)/dimer B2" molar ratio required to obtain at least 2.5%, preferably at least 5%, more preferably at least 10%, in particular at least 25%, and for example at least 40%, of furan-flavan monomer compounds of general formula (I) relative to the total of the compounds (furan-flavan monomers of general formula (I) and terminal units) formed during a reaction of depolymerization of the dimer B2 by the nucleophile of general formula (III) in the presence of hydrochloric acid at 0.1 N in methanol, at 30° C. and in a reaction time of 10 minutes.

The amount of depolymerizable condensed tannins in a sample of condensed tannins can be determined by any method known to those skilled in the art, for example by carrying out, on this sample, a depolymerization process by means of a nucleophile such as phloroglucinol or 2-mercaptoethanol, known to be capable of quantitatively depolymerizing depolymerizable condensed tannins, and by measuring the amount of condensed tannins thus depolymerized, which correspond substantially to the amount of depolymerizable condensed tannins initially present in the sample. The molarity of the tannins is conventionally expressed in equivalents of simple, non-galloylated monomers.

With respect to this amount of depolymerizable condensed tannins, the molar amount of nucleophile of general formula (III) to be used in the method according to the invention is preferentially determined by comparison with a depolymerization reaction carried out on the dimer B2 by means of said nucleophile of general formula (III).

The dimer B2, or epicatechin-(4β→8)-epicatechin, is a model tannin well known to those skilled in the art, and commercially available, in particular from the suppliers Sigma-Aldrich or ExtraSynthése.

The implementation of a reaction for depolymerization of the dimer B2 at 0.7 mmol.l$^{-1}$, using the nucleophile of general formula (III) at a given molar concentration, in the presence of hydrochloric acid at 0.1 N in methanol and at 30° C., makes it possible to establish, for example by chromatography analysis, in particular by ultra performance liquid chromatography (UPLC), the amount, on the one hand, of furan-flavan monomers of general formula (I) and, on the other hand, of terminal units of the dimer, obtained in a reaction time of 10 minutes. The implementation of such a reaction for various concentrations of nucleophile of general formula (III) makes it possible to determine which molar concentrations of this nucleophile make it possible to obtain at least 2.5%, preferably at least 5%, more preferably at least 10%, in particular at least 25%, and for example at least 40%, of furan-flavan monomers of general formula (I), relative to the total of furan-flavan monomers of general formula (I) and of terminal units obtained.

It has been discovered by the present inventors that a "nucleophile of general formula (III)/depolymerizable condensed tannins" molar ratio greater than or equal to a "nucleophile of general formula (III)/dimer B2" molar ratio thus determined advantageously makes it possible to obtain high depolymerization reaction yields in a reduced time, by limiting in particular the effect of competition of the nucleophilic monomer forms of the tannins with the nucleophile of general formula (III) in accordance with the present invention.

The "nucleophile of general formula (III)/depolymerizable condensed tannins" molar ratio, for which the molarity of the tannins is expressed in equivalents of simple, non-galloylated monomers, is in particular preferentially greater than or equal to 133, for example greater than or equal to 200 for furan, and greater than or equal to 1.67, for example greater than or equal to 20 for sylvan. Such molar ratios make it possible to obtain high yields of the depolymerization reaction, in particular greater than or equal to 85%.

In particular embodiments of the invention, for carrying out the depolymerization step using the furan as nucleophile, the initial ratio expressed in moles of nucleophile per gram of depolymerizable condensed tannins is preferably greater than or equal to 1.72, and preferentially greater than or equal to 3.44. Such a characteristic makes it possible to advantageously obtain a production yield for the compound of general formula (I) according to the invention of greater than or equal to 90%. Throughout the present description, the yield of the depolymerization reaction according to the invention is expressed as percentage of the reference values obtained by a standard depolymerization reaction, using 2-mercaptoethanol as nucleophilic reagent, termed thiolysis, described in particular in the publication by Roumeas et al., 2013.

When the nucleophile of general formula (III) is sylvan, a minimum ratio of 0.555 mol of sylvan per gram of depolymerizable condensed tannins makes it possible to obtain a yield close to 100%, and the value of this ratio can be lowered to 0.139 while at the same time retaining a yield of at least 90%.

In particular embodiments of the invention, which are particularly adapted to the use of furan as nucleophile for the condensed tannin depolymerization step, the concentration of depolymerizable condensed tannins subjected to the depolymerization step is less than or equal to 5 g/l. Concentrations in such a range prove to be particularly advantageous in terms of absence of formation of by-products and also of quantitative yield of the reaction.

In other particular embodiments of the invention, which are particularly adapted to the use of sylvan as nucleophile for the condensed tannin depolymerization step, the concentration of depolymerizable condensed tannins subjected to the depolymerization step is less than or equal to 80 g/l. Concentrations in such a range prove to be particularly advantageous in terms of absence of formation of by-products and also of quantitative yield of the reaction.

The acid used for the condensed tannin depolymerization step may be of any type. It is in particular chosen from acids commonly used in the industrial field, such as sulfuric acid ($H_2SO_4$), hydrochloric acid (HCl), methanesulfonic acid (MsOH), formic acid and acetic acid, or a mixture of such acids. Acids attached to a solid support, such as of Amberlyst® 15 type, are particularly preferred in embodiments of the method in continuous flow, for extracts of condensed tannins that are soluble under the reaction conditions.

The concentration of acid used in the condensed tannin depolymerization step is preferably equivalent to the concentration of this acid required to confer a pH of between −1 and 3.5 on an aqueous solution. It is within the competence of those skilled in the art to determine, for each particular acid, the appropriate concentration range.

By way of example, when the acid is hydrochloric acid, it can be introduced into the reaction medium, for carrying out the depolymerization step, in a concentration of between 0.1 and 2.0 mol/l. More generally, for this acid, as for methanesulfonic acid, concentrations of between 0.1 and 0.4 mol/l are particularly preferred.

In particular embodiments of the invention, the depolymerization step is carried out in a polar solvent, preferably a protic solvent, such as for example methanol, ethanol, formic acid or acetic acid, or in a mixture of solvents containing at least one polar, preferably protic, solvent. In the latter case, the solvents used in the mixture are advantageously chosen so as to be inert with respect to one another under the reaction conditions. Where appropriate, the polar solvent(s), where appropriate protic solvent(s), may be as a mixture with one or more solvents of other types, including aprotic or nonpolar solvents.

The proportion of the nucleophile of general formula (III) in the solvent can then be between 1% and 75% by volume, preferably between 10% and 75% by volume, relative to the volume of solvent, preferentially be approximately equal to 25% by volume relative to the volume of solvent.

The condensed tannin depolymerization step is preferably carried out at a temperature below or equal to the boiling point of the nucleophile of general formula (III) at the pressure applied in the reactor, and where appropriate, when a solvent is added to the reaction medium, at a temperature below or equal to the boiling point of this solvent at this same pressure. By way of example, when the reaction is carried out at atmospheric pressure, temperatures of between 30° C. and 40° C. are particularly preferred.

Generally, the depolymerization step of the method according to the invention can advantageously be carried out with a high yield, of at least 90%, in a time as short as 30 minutes, or a few hours depending on the nucleophile used, this being at a moderate temperature, in particular below 50° C.

By way of example, when the nucleophile is furan of formula (IIIa), one or more of the following operating parameters can be applied:
initial concentration: 1 g/l of condensed tannins
solvent: methanol
volume ratio of furan in methanol: 25% v/v
acid: hydrochloric acid at 0.1 mol/l
temperature: 30° C.

Such operating conditions prove to be entirely advantageous in terms of yield and rate of the depolymerization reaction. They make it possible for example to achieve a yield as high as 100% starting from an industrial extract of seed tannins from marcs from white wine vinification or a model tannin, the dimer B2 (epicatechin-(4β→8)-epicatechin).

Under these same conditions, but with an initial concentration of 0.2 g/l of dimer B2, the method according to the invention also makes it possible in particular to depolymerize the dimer B2 in a very short time, of 10 minutes.

The method according to the invention can comprise a final step of separating out of the reaction medium the compound of general formula (I) that it makes it possible to obtain. This separation is in particular carried out rapidly at the end of the reaction, so as to avoid any phenomenon of degradation of the compound formed in the acidic reaction medium. It can be carried out by any technique that is conventional in itself. For example, it can consist in adding water to the medium, in evaporating off the solvents and the nucleophile by vacuum evaporation, and then in extracting the products of interest by liquid/liquid extraction using a water-immiscible organic solvent, such as ethyl acetate, diethyl ether, etc.

The method according to the invention can be carried out batchwise. Preferentially, for the depolymerization of a tannin extract that is soluble in the reaction mixture, it is carried out in continuous flow, by means of a facility that is conventional in itself in the industrial field.

When the method according to the invention is carried out in continuous flow, for example in a thermostated reactor, the acid is preferably supported, so as to be easily separable by filtration.

In the case of the direct treatment of the biomass, the method can for example be carried out by means of a solvent/reagent co-current, twin-screw extruder, that is conventional in itself, comprising a first segment allowing milling of the raw material, and a second segment allowing the addition of the solvents/reagents, with blending and impregnation. The reaction time is set by the speed of the extruder. In a third segment, the spin-drying and the filtration of the products of interest are carried out. An example of such an extruder for treating biomass is in particular described in the handbook by Maréchal, 2001.

The acid can then be neutralized and/or washed with water, the solvents and reagents can be evaporated off under vacuum or distilled at atmospheric pressure, and the products of interest can be taken up with an organic solvent such as ethyl acetate, diethyl ether, etc.

The compound of general formula (I) according to the invention can otherwise be obtained by any other process, in particular by furylation of flavan monomers obtained from condensed tannins or from any other type of tannins by any other method, or else by furylation of chemically obtained compounds.

For example, starting from taxifolin of formula (IV) below, it is possible to carry out a first step of in situ reduction of the carbonyl function, so as to obtain the corresponding 3,4-diol derivative (V), for example according to the following reaction scheme:

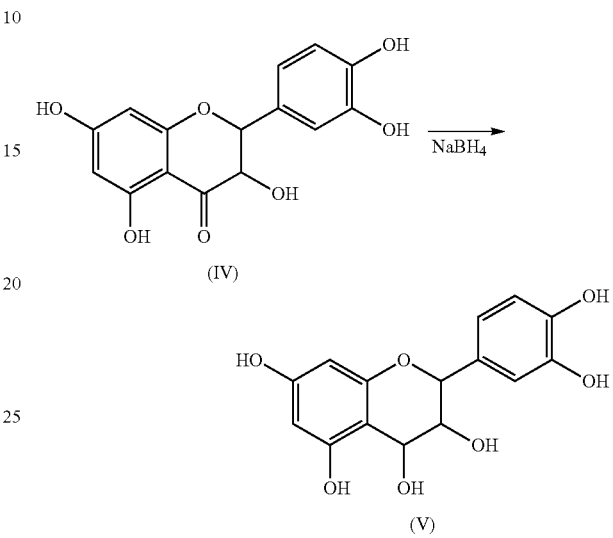

In a second step, the 3,4-diol derivative (V) obtained can be brought into contact with a nucleophile of general formula (III) according to the invention, in an acidic medium, in the same way as that described above with reference to the condensed tannin depolymerization method, so as to obtain the compound of general formula (I) according to the invention. This reaction scheme can also be applied to taxifolin and/or its reduction product, the 3,4-diol derivative, the phenolic hydroxyl groups of which having been protected beforehand.

Another aspect of the invention relates to the use, for depolymerizing condensed tannins, of a compound of general formula (III):

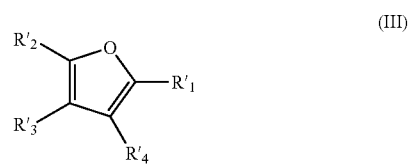

in which $R'_1$, $R'_2$, $R'_3$ and $R'_4$, which may be identical or different, each represent a hydrogen atom or a substituent not comprising any mesomeric-effect electron-withdrawing group conjugated to the furan nucleus, at least one substituent among $R'_1$, $R'_2$, $R'_3$ and $R'_4$ representing a hydrogen atom.

$R'_1$, $R'_2$, $R'_3$ and $R'_4$ may in particular correspond to one or more of the features set out above with reference to general formula (III).

BRIEF DESCRIPTION OF THE DRAWINGS

The features and advantages of the invention will emerge more clearly in the light of the examples below, which are given simply by way of illustration and are in no way limiting of the invention, with the support of FIGS. 1 to 8, in which:

FIG. 6 shows UPLC chromatograms, with detection at 280 nm, carried out on an aqueous solution of the products resulting from the depolymerization of a condensed tannin extract by thiolysis, (a) before, and (b) after, bringing into contact for 19 h with a buffer solution at pH 9;

FIG. 7 shows UPLC chromatograms, with detection at 280 nm, carried out on an aqueous solution of a crude product resulting from the depolymerization of a condensed tannin extract using sylvan in accordance with one particular embodiment of the invention, (a) before, and (b) after, bringing into contact for 19 h with a buffer solution at pH 9; and FIG. 8 shows sigmoid curves established from the various experimental results, expressing the molar ratio between the derivatives derived from the extension units $U_{ext}$ and the total of the extension units and of the terminal units $U_{term}$ ($U_{ext}/(U_{ext}+U_{term})$), as a function of the "nucleophile/dimer B2" initial molar ratio, for experiments in which the dimer B2 was depolymerized using the nucleophiles in accordance with the invention, furan and sylvan, for initial concentrations of dimer B2 of 100, 200 or 400 mg.l$^{-1}$, and various initial nucleophile concentrations.

DETAILED DESCRIPTION OF THE EMBODIMENTS

Materials and Methods

Figure 1:
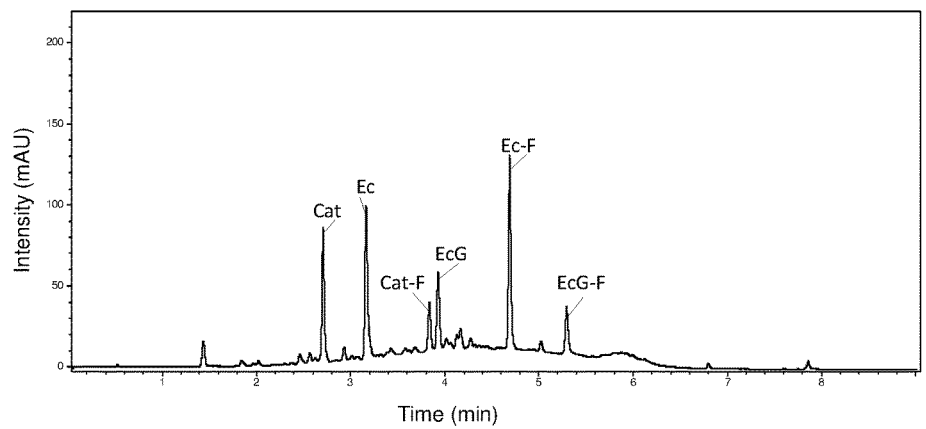
FIG. 1 shows a UPLC chromatogram at 280 nm of the reaction crude obtained after carrying out a condensed tannin depolymerization method according to one particular embodiment of the present invention (furanolysis), using hydrochloric acid (HCl) as acid.

For the experiments below, the solvents and reagents were obtained from Sigma-Aldrich for the furan, the sylvan, the 2-mercaptoethanol, the anhydrous methanesulfonic acid (MsOH) and the catechin; from Carl Roth for the fuming hydrochloric acid (HCl 37% aq.); and from ProLabo for the methanol (analytical grade) (MeOH) and the absolute ethanol (EtOH). The "hydrochloric" and "methanesulfonic" solutions are prepared respectively by a dilution of fuming HCl (37% aq.) and of MsOH in the solvent concerned.

The industrial seed condensed tannin extracts produced from marcs originating from vinifications into white wines ("white seed tannins") (high quality grade) were obtained from the Union des Distilleries de la Méditerranée [Union of Mediterranean Distilleries], and the dimer B2 from the company Extrasynthése.

General Protocol for Analyzing the Depolymerization Reaction Products (Identification and Quantification)

The analysis consists in carrying out a separation of the depolymerization reaction products by ultra performance liquid chromatography (Waters UPLC system) coupled in series to a diode array detector (DAD) and to a mass spectrometer (Brucker AmaZonX model) (UPLC-MS). The samples resulting from the depolymerization are analyzed extemporaneously, without pretreatment, the reaction medium being diluted, where appropriate, for a final tannin concentration at 1 g.l$^{-1}$ (200 mg.l$^{-1}$ for the dimer B2). The samples (2 µl) are injected on to a Waters Acquity Atlantis HSS T3 1.8 µm–2.1×100 mm column, and eluted with the solvents A ($H_2O$:HCOOH 99:1) and B ($H_2O$:HCOOH: MeCN 19:1:80), according to the A/B gradient: 99.9% to 60% linear, 5 min; 60% to 1% linear, 2 min; 1% isocratic, 1 min; 1% to 99.9% linear, 1 min. The UV chromatogram recorded at 280 nm allows the quantitative analysis by integration of the peaks corresponding to each of the products, by virtue of a prior external calibration of the reaction products. The MS(+) chromatogram allows the identification of the products, on the basis of the m/z values.

A preparative separation by flash chromatography on a "DIOL" grafted silica column (Interchim), followed where appropriate by a semi-preparative chromatography (C18 grafted silica), makes it possible to isolate the products with a high purity in order to confirm the structures by NMR and to determine their coefficients of response on the UPLC-MS apparatus.

For each kinetics undertaken, the quantification of the reagents and of the products is carried out by UPLC-MS(+) analysis. To this effect, as soon as the reagents are brought together, the reaction mixture is immediately distributed by sampling one and the same volume in several tubes. All the samples are placed in a thermostated bath and brought to the selected temperature. One sample is sacrificed for each point of the time course corresponding to a given time. Once removed from the bath, the sample is cooled to 10° C., diluted if necessary and injected extemporaneously into the chromatograph.

EXAMPLE 1

Comparative Study of Processes for Thiolysis or for Furanolysis of White Seed Tannins at 1 g/l The polymerization of an extract of white seed tannins was carried out in an acidic medium by means, on the one hand, of a sulfur-bearing nucleophile as proposed by the prior art (analytical thiolysis reaction, comparative example) and, on the other hand, of a nucleophile in accordance with the present invention, furan (furanolysis reaction), in the presence respectively of two different acids, hydrochloric acid and methanesulfonic acid.

Thiolysis (Comparative Example)

An optimized thiolysis reaction, according to the protocol described in the publication by Roumeas et al., 2013, is carried out in the following way.

In a 10 ml tube, the tannin extract (10 mg) is dissolved in methanol (MeOH) (5 ml), then 5 ml of the thiolytic depolymerization solution (12 µl of 2-mercaptoethanol and 83 µl of fuming HCl per 5 ml of MeOH qs) are added. The tube is closed with a phenolic stopper equipped with a PTFE septum, and left to stir at 40° C. for 2 h.

Furanolysis—HCl

A first furanolysis reaction in accordance with the present invention is carried out as follows.

In a 10 ml tube, the tannin extract (10 mg) is dissolved in MeOH (5 ml), then the furan (2.5 ml) and a hydrochloric solution of MeOH (0.4 mol.l$^{-1}$) are added. The tube is closed with a phenolic stopper equipped with a PTFE septum, and left to stir at 40° C. for 1 h.

Furanolysis—MsOH

A second furanolysis reaction in accordance with the present invention is carried out as follows.

In a 10 ml tube, the tannin extract (10 mg) is dissolved in MeOH (5 ml), then furan (2.5 ml) and the solution of MsOH at 0.4 mol.l$^{-1}$ in MeOH (5 ml) are added. The tube is closed with a phenolic stopper equipped with a PTFE septum, and left to stir at 40° C. for 1 h.

In the grape, since a proportion of the constituent units of the polymer chains forming the tannins are galloylated, that is to say esterified with gallic acid at the level of the hydroxyl radical in the C3 position, the depolymerization reactions result in the formation of the following products:

furylated extension units corresponding to general formula (I) according to the invention:

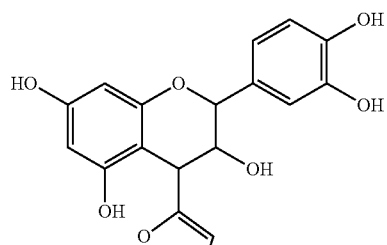

Derivative

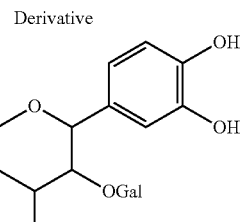

Galloylated derivative terminal units:

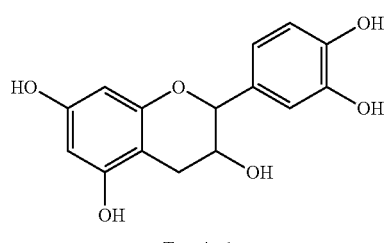

Terminal

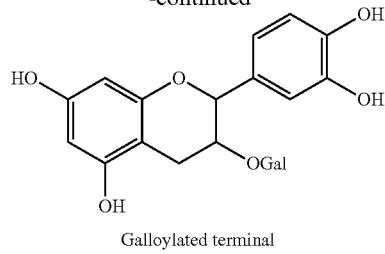

Galloylated terminal wherein Gal represents a gallate group of formula (II) defined above.

For each of the depolymerization reactions, the amount of each of the products formed is determined by UPLC-MS, as indicated above. The depolymerization products are referenced as follows: catechin terminal units (Cat), epicatechin terminal units (Ec), epicatechin gallate terminal units (EcG), and furylated extension units of catechin (Cat-F), of epicatechin (Ec-F) and of epicatechin gallate (EcG-F).

By way of example, FIG. 1 shows the UPLC chromatogram at 280 nm of the reaction crude obtained at the end of the furanolysis—HCl reaction described above.

For each of the products formed, the retention time and the m/z value observed by MS(+) are indicated in table 1 below.

TABLE 1

UPLC retention time and m/z values observed by MS(+) of the depolymerization products obtained by means of a furanolysis - HCl method in accordance with the invention

| Product | Retention time (min) | (M + H$^+$) |
|---------|----------------------|-------------|
| Cat     | 2.8                  | 291         |
| Ec      | 3.2                  | 291         |
| EcG     | 4.0                  | 443         |
| Cat-F   | 3.9                  | 357         |
| Ec-F    | 4.7                  | 357         |
| EcG-F   | 5.3                  | 509         |

Figure 2:
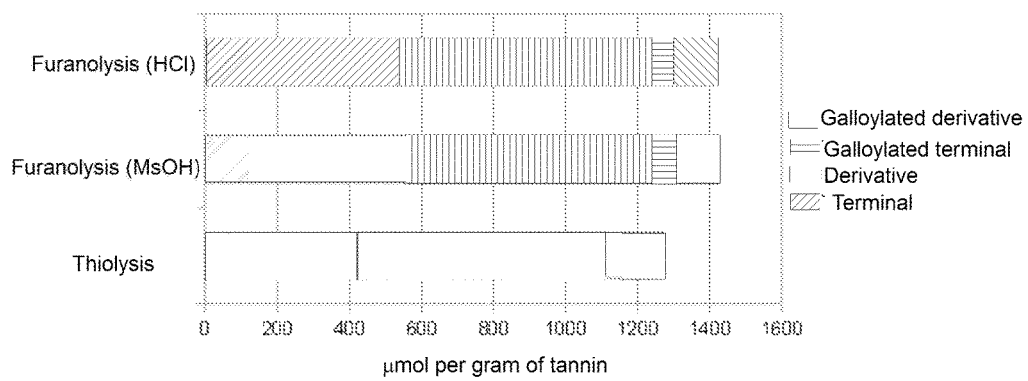
FIG. 2 represents a graph showing the amounts of each of the reaction products, per gram of tannins treated, for condensed tannin depolymerization methods according to particular embodiments of the present invention (furanolysis), using hydrochloric acid (HCl) or methanesulfonic acid (MsOH) as acid, and also for a tannin depolymerization reaction using a sulfur-bearing nucleophile proposed by the prior art (thiolysis)

The amounts of each of the reaction products formed per gram of tannins are deduced from this analysis, for each of the processes described above. The results obtained are shown in FIG. 2.

It is observed that the reactions carried out with furan as nucleophile, in accordance with the present invention, give results similar to the depolymerization reactions of the prior art by optimized thiolysis, and with a yield that is even better with regard to the terminal units.

Moreover, no significant difference is observed between the use of HCl or of MsOH as acid catalyst.

EXAMPLE 2

Depolymerization by Furanolysis of Douglas Pine Tannins

The pine bark lipids (5 g) are extracted with 3×50 ml of hexane. The tannins are then extracted with a 70/30/0.05 v/v/v acetone/H$_2$O/TFA mixture (3×50 ml). The acetone is evaporated off under vacuum, and the aqueous phase is then lyophilized to give 900 mg of tannin extract in the form of a brownish powder.

A method for depolymerization of the tannins thus obtained in accordance with the invention is carried out as follows.

In a tube, the tannins (100 mg) are dissolved in MeOH (72.5 ml), and then furan (25 ml) and a hydrochloric methanol solution at 4.0 mol.l$^{-1}$ (2.5 ml) are added. The tube is closed with a phenolic stopper equipped with a PTFE septum, and left to stir at 40° C. for 1 h.

The yields evaluated on the basis of a UPLC-MS analysis, as indicated above, are greater than or equal to those obtained by means of an analytical thiolysis (that is to say 440 μmol of furylated derivatives per gram of extract).

EXAMPLE 3

Furanolysis of the Dimer B2

The dimer B2 was subjected to a depolymerization step in accordance with the present invention, at several concentrations, according to the following reaction conditions.

For each test, the kinetics of the depolymerization reaction is monitored over time by determination by UPLC-MS, as described above, of the concentrations of unreacted dimer B2 and of reaction products formed.

10 g.l$^{-1}$ 15 mg of dimer B2 are dissolved in MeOH (1.12 ml), then furan (375 μl) and then fuming HCl (12.5 μl) are added. The solution (180 μl) is transferred into 300 μl vials, which are sealed with aluminum capsules with a septum, and brought to 40° C. The reaction is monitored by UPLC-MS(+) for 8 h.

1 g.l$^{-1}$ 1.5 ml of solution of dimer B2 at 1.0 g.l$^{-1}$ are prepared in a 25% v/v furan/MeOH mixture. The hydrochloric acid (12.5 μl) is added. 180 μl of solution are transferred into 300 μl vials, which are sealed with aluminum capsules with a septum, and brought to 40° C. The reaction is monitored by UPLC-MS(+) for 8 h.

0.2 g.l$^{-1}$ 1.5 ml of solution of dimer B2 at 200 mg.l$^{-1}$ are prepared in a 25% v/v furan/MeOH mixture. The hydrochloric acid (12.5 μl) is added. 180 μl of solution are transferred into 300 μl vials, which are sealed with aluminum capsules with a septum, and brought to 40° C. The reaction is monitored by UPLC-MS(+) for 180 min.

Figure 3:
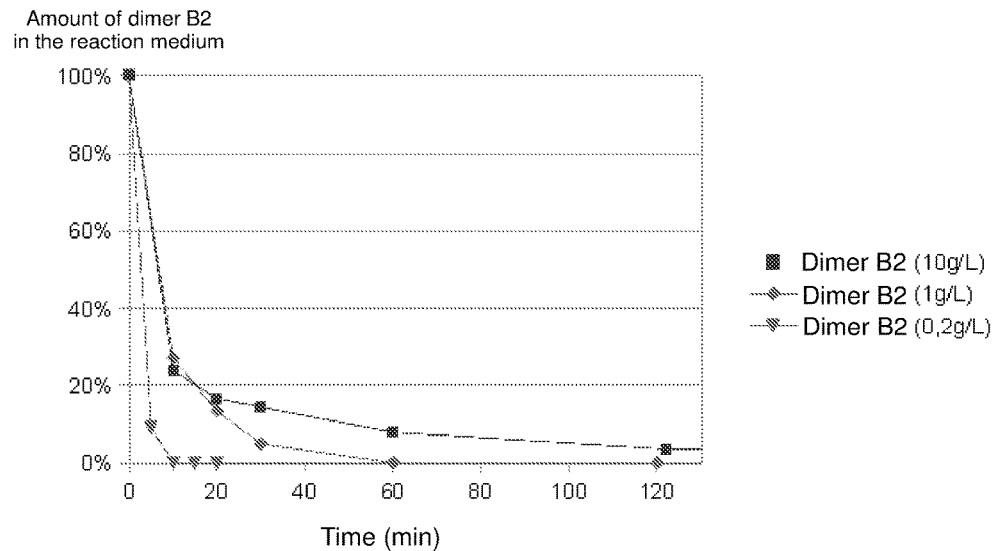
FIG. 3 represents a graph showing the effect of the initial concentration of dimer B2 on its kinetics of disappearance during a method, in accordance with one embodiment of the invention, of furanolysis of a commercial preparation of dimer B2 in the presence of a methanolic solution of furan (25% v/v) and of HCl (0.1 mol.l$^{-1}$)
Figure 4:
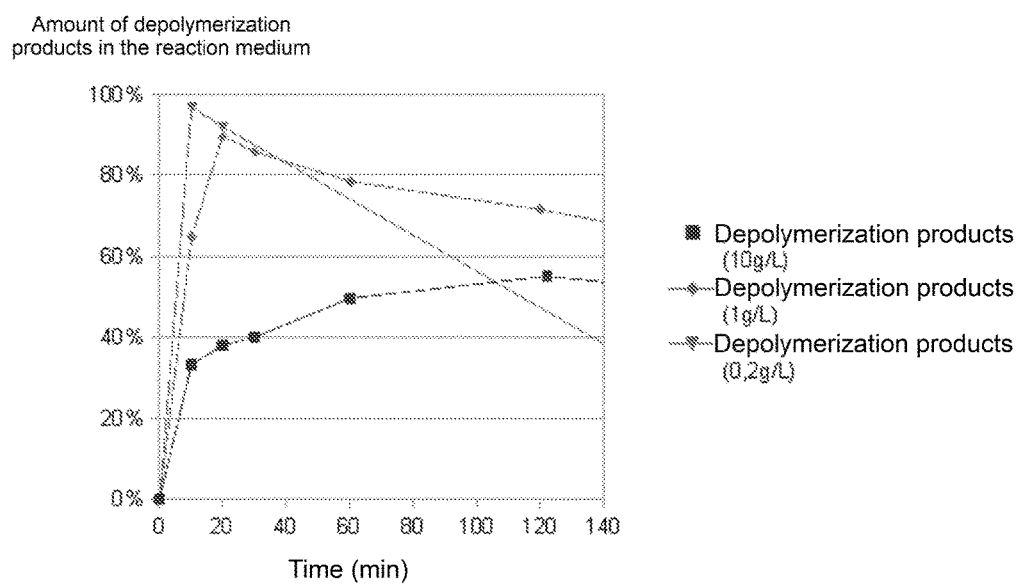
FIG. 4 represents a graph showing the effect of the initial concentration of dimer B2 on the kinetics of appearance of the depolymerization products during the furanolysis method having been carried out for obtaining FIG. 3.

For each initial concentration of dimer B2, the results obtained are shown in FIG. 3, for the dimer B2 disappearance kinetics, and in FIG. 4, for the depolymerization product appearance kinetics.

It is noted that the maximum amount of depolymerized units represents 90% and 97% of the initial amount of dimer B2, respectively for initial concentrations of 0.2 g/l and 1.0 g/l. These maximum amounts are obtained in very short reaction times, respectively of 10 min and 20 min. In comparison, lower yields are obtained when the initial concentration of dimer B2 is equal to 10 g/l, since the maximum amount of depolymerized units then represents 55% of the initial amount of dimer B2. In addition, the lower the initial concentration of dimer B2, the faster the appearance of the depolymerization products.

For a dimer B2 concentration of 10 g/l, the apparent kinetics of disappearance of the dimer B2 is in addition slower than the apparent rate of appearance of the depolymerized units. The difference in kinetics observed between the appearance of the depolymerization products and the disappearance of the dimer B2 suggests that the depolymerization products and the dimer B2 become competitive nucleophiles with respect to the furan at a high concentration of flavan units in the medium, that is to say at high concentrations of the dimer itself and its depolymerization products. These observations appear to indicate a reaction scheme involving numerous elementary reactions, and demonstrate the advantage of proceeding, when the nucleophile is the furan, and as recommended by the present invention, under dilute conditions, that is to say at low initial concentrations of condensed tannins in the reaction medium, of less than 10 g/l.

EXAMPLE 4

Furanolysis of White Seed Tannins Using the Furan in Ethanol

A method for depolymerizing white seed tannins is carried out in accordance with the present invention, by means of furan as nucleophile, in ethanol as solvent, according to the following operating protocol.

A solution of tannin sample at 2 g.l$^{-1}$ in absolute ethanol (EtOH), and the furanolysis solution (50% v/v furan in methanesulfonic EtOH at 0.2 mol.l$^{-1}$) are prepared. The reaction mixture is prepared by adding 1.0 ml of each solution to an Eppendorf tube, then 200 μl of solution are transferred into 300 μl vials, which are sealed with aluminum capsules with a septum, and brought to 40° C. The reaction is monitored by UPLC-MS(+) for 80 min. The maximum yield, obtained after 40 min of reaction, is 510 μmol of depolymerization products per gram of extract (that is to say 73% of the estimated maximum value by thiolysis).

EXAMPLE 5

Furanolysis of White Seed Tannins with Furan—Influence of the Furan/Tannin Ratio Methods for depolymerizing white seed tannins are carried out in accordance with the present invention, by means of furan as nucleophile, with several different "moles of furan/weight of tannins" ratios, according to the following operating protocol.

The white seed tannin extract is dissolved in MeOH (12 ml). The furan (4 ml) and then the fuming hydrochloric acid (133 μl) are added. This solution is distributed into 8 Eppendorf tubes, in a proportion of 1.5 ml per tube. Each tube is closed with Parafilm® and brought to 30° C. The reaction kinetics are monitored by UPLC-MS(+) for 8 h.

The operating conditions and results obtained are shown in table 2 below.

TABLE 2

Operating conditions and yield of a reaction of furanolysis of white seed tannins with furan in accordance with the invention

| Tannin concentration (g/l) | "Moles of furan/g of tannins" ratio | "Moles of furan/moles of tannin eq. monomers" ratio | Max. yield (μmol · g$^{-1}$ of tannins) | Max. yield (compared with analytical thiolysis) | Time for obtaining max. yield |
|---|---|---|---|---|---|
| 1 | 3.44 | 1000 | 702 | 100% | 1 h 30– 6 h |
| 2 | 1.72 | 500 | 652 | 93% | 1 h 30– 8 h |
| 3 | 1.15 | 334 | 611 | 87% | 1 h 30– 8 h |
| 5 | 0.688 | 200 | 610 | 87% | 4 h 30 |
| 10 | 0.344 | 100 | 461 | 66% | 4–8 h |

These tests show that, when the nucleophile is furan, high reaction yields can be obtained for all the tannin concentrations tested. These yields are highest for tannin concentrations of less than or equal to 5 g.l$^{-1}$.

EXAMPLE 6

Depolymerization of White Seed Tannins with Sylvan—Influence of the Sylvan/Tannin Ratio Methods for depolymerizing white seed tannins are carried out in accordance with the present invention, by means of sylvan as nucleophile, with several different "moles of sylvan/weight of tannins" ratios, according to the following operating protocol.

The white seed tannin extract is dissolved in MeOH (12 ml). The sylvan (4 ml) and then fuming hydrochloric acid (133 μl) are added. This solution is distributed into 8 Eppendorf tubes, in a proportion of 1.5 ml per tube. Each tube is closed with Parafilm® and brought to 30° C. The reaction kinetics are monitored by UPLC-MS(+) for 4 h.

The depolymerization products are referenced as follows: catechin terminal units (Cat), epicatechin terminal units (Ec), epicatechin gallate terminal units (EcG), and sylvanylated extension units of catechin (Cat-S), of epicatechin (Ec-S) and of epicatechin gallate (EcG-S).

Figure 5:
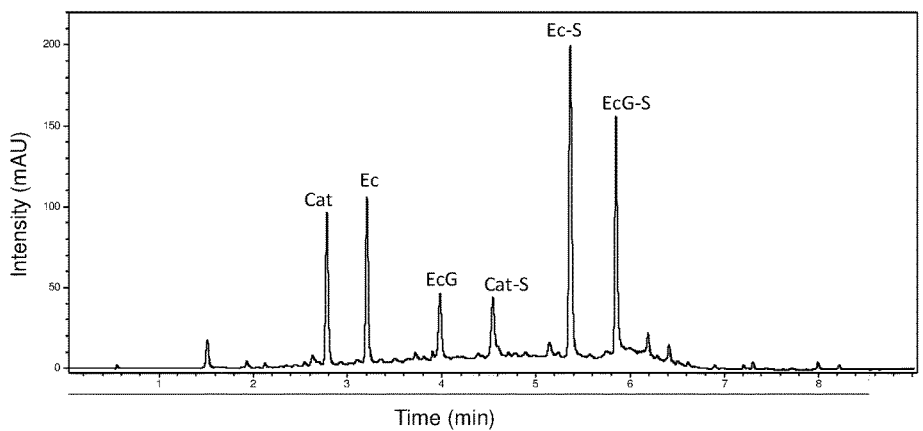
FIG. 5 shows a UPLC chromatogram at 280 nm of the reaction crude obtained after carrying out a condensed tannin depolymerization method according to one particular embodiment of the present invention (sylvanolysis), using hydrochloric acid (HCl) as acid.

FIG. 5 shows the UPLC chromatogram obtained after 1 h of reaction.

For each of the products formed, the retention time and the m/z value observed by MS(+) are indicated in table 3 below.

TABLE 3

UPLC retention time and m/z values observed by MS(+) of the depolymerization products obtained by means of a sylvanolysis - HCl method in accordance with the invention

| Product | Retention time (min) | (M + H$^+$) |
|---|---|---|
| Cat | 2.8 | 291 |
| Ec | 3.2 | 291 |
| EcG | 4.0 | 443 |
| Cat-S | 4.5 | 371 |
| Ec-S | 5.4 | 371 |
| EcG-S | 5.9 | 523 |

The operating conditions and results obtained, in terms of yield, are indicated in table 4 below.

TABLE 4

Operating conditions and yield for a reaction of depolymerization of white seed tannins with sylvan in accordance with the invention

| Tannin concentration (g/l) | "Moles of sylvan/g of tannins" ratio | "Moles of sylvan/moles of tannin eq. monomers" ratio | Max. yield. (μmol · g$^{-1}$ of tannins) | Max. yield (compared with analytical thiolysis) | Time for obtaining max. yield |
|---|---|---|---|---|---|
| 1 | 2.77 | 800 | 720 | 103% | 30 min-1 h 30 |
| 5 | 0.555 | 160 | 730 | 104% | 30 min-2 h |
| 10 | 0.277 | 80 | 650 | 93% | 60 min |
| 20 | 0.139 | 40 | 662 | 95% | 45 min-1 h 30 |
| 40 | 0.069 | 20 | 626 | 89% | 45 min-1 h 30 |
| 80 | 0.035 | 10 | 581 | 83% | 90 min |
| 1 | 0.0035 | 1 | 329 | 47% | 4-6 h |

These tests show that, when the nucleophile is sylvan, very high reaction yields can be obtained for all the tannin concentrations tested.

EXAMPLE 7

Preparative Depolymerization of White Seed Tannins with Furan

A depolymerization method in accordance with the invention is carried out in the following way.

In a bottle, the tannin extract (5.0 g) is dissolved in MeOH (200 ml), then the furan (108 ml), and then the hydrochloric methanol (83 ml of fuming HCl in 108 ml of MeOH) are added without stirring. The mixture is brought to 40° C., for 30 min, and then cooled to 0° C. 500 ml of an aqueous solution of Na$_2$CO$_3$ (106 g.l$^{-1}$) are then added. The mixture is extracted with ethyl acetate (AcOEt) (3×400 ml), then subjected to evaporation. A pasty brown-black solid is obtained (3.34 g), which is taken up in diethyl ether (Et$_2$O) (200 ml), triturated and sonicated, and then washed with brine (300 ml). These operations are repeated twice, and the solutions obtained are dried (Na$_2$SO$_4$) and then evaporated so as to obtain a brownish pasty solid (2.40 g), which consists of a mixture of terminal units and of furylated extension units.

The product thus obtained is purified by flash chromatography. The mixture (150 mg) is dissolved in Et$_2$O (5 ml), and is then injected on to a DIOL column and eluted with an AcOEt/Et$_2$O gradient (from 0 to 50%). The fractions of interest (furylated extension units) are combined and evaporated under vacuum. 54 mg of the furylated flavan monomer below are obtained:

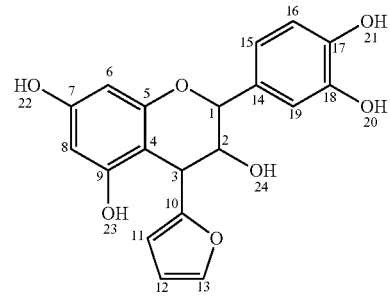 [SMILES: Oc1cc(O)c2c(c1)OC(c1ccc(O)c(O)c1)C(O)C2c1ccco1]

The NMR data obtained for this compound, indicated in table 5 below, confirm the structure above.

TABLE 5

NMR characterization of the furylated derivative obtained by means of a depolymerization method according to the invention

| Attribution | $^{13}$C (ppm) | Type | $^{1}$H (ppm) | J (Hz) |
|---|---|---|---|---|
| 1 | 74.4 | CH | 4.57 | sl |
| 2 | 68.4 | CH | 3.94 | m |
| 3 | 39.1 | CH | 4.07 | m |
| 4 | 98.2 | Q | — | — |
| 5 | 155.9 | Q | — | — |
| 6 | 94.0 | CH | 5.78 | d-2.1 Hz |
| 7-9-10 | 157.3-157.1-157.0 | Q | — | — |
| 8 | 95.4 | CH | 5.92 | d-2.1 Hz |
| 11 | 106.6 | CH | 5.80 | d-2.9 Hz |
| 12 | 110.3 | CH | 6.34 | dd-1.7/2.9 Hz |
| 13 | 141.4 | CH | 7.55 | d-1.7 Hz |
| 14 | 130.1 | Q | — | — |
| 15 | 117.7 | CH | 6.51 | dd-1.7/8.1 Hz |
| 16 | 114.9 | CH | 6.66 | d-8.1 Hz |
| 17-18 | 144.7-144.6 | Q | — | — |
| 19 | 114.7 | CH | 6.81 | d-1.7 Hz |
| 20-21 | | OH | 8.72-8.82 | s |
| 22 | | OH | 9.04 | s |
| 23 | | OH | 9.15 | s |
| 24 | | OH | 5.08 | d-4.7 Hz |

The positions of the aromatic groups are moreover confirmed by $^{13}$C-$^{1}$H HMBC heteronuclear two-dimensional NMR.

EXAMPLE 8

Preparative Depolymerization of White Seed Tannins with Sylvan

A depolymerization method in accordance with the invention is carried out in the following way.

In a round-bottomed flask, the tannin extract (8.0 g) is dissolved in MeOH (300 ml), then sylvan (100 ml), and then gently fuming HCl (3.33 ml), are added with stirring. The mixture is brought to 30° C. for 60 min. 400 ml of an aqueous solution of Na$_2$CO$_3$ (5.3 g.l$^{-1}$) are added and then an extraction is carried out with AcOEt (3×400 ml). The solution is evaporated so as to give a pasty brownish solid (5.7 g), which is taken up with Et$_2$O (200 ml), triturated and sonicated, and then washed with brine (300 ml). These operations are repeated twice, and the resulting solutions are combined, and dried with Na$_2$SO$_4$. The solution is evaporated so as to obtain a bullate beige solid (2.40 g), consisting of a mixture of terminal units and of sylvanylated extension units.

The product thus obtained is purified by flash chromatography. The mixture (300 mg) is dissolved in Et$_2$O (5 ml), and is then injected on to a DIOL column and eluted with an AcOEt/Et$_2$O gradient (from 0 to 50%). The fractions of interest (sylvanylated extension units) are combined and evaporated under vacuum. 99 mg of the sylvanylated flavan monomer below are obtained:

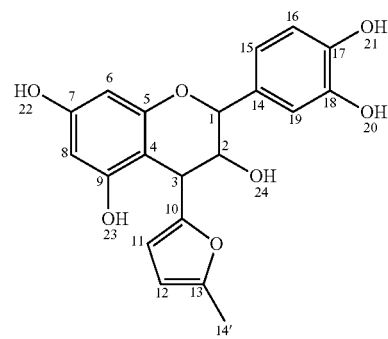 [SMILES: Cc1ccc(C2c3c(O)cc(O)cc3OC(c3ccc(O)c(O)c3)C2O)o1]

The NMR data obtained for this compound, indicated in table 6 below, confirm the structure above.

TABLE 6

NMR characterization of the sylvanylated derivative obtained by means of a depolymerization method according to the invention

| Attribution | $^{13}$C (ppm) | Type | $^{1}$H (ppm) | J (Hz) |
|---|---|---|---|---|
| 1 | 74.3 | CH | 4.61 | sl |
| 2 | 68.4 | CH | 3.92 | m |
| 3 | 39.1 | CH | 4.03 | m |
| 4 | 98.2 | Q | — | — |
| 6 | 94.0 | CH | 5.77 | d-2.5 Hz |
| 5-7-9-10 | 157.3-157.0-156.0-155.3 | Q | — | — |
| 8 | 95.3 | CH | 5.92 | d-2.3 Hz |
| 11 | 106.3 | CH | 5.92 | d-2.5 Hz |
| 12 | 107.3 | CH | 5.62 | d-2.5 Hz |
| 13 | 149.8 | Q | — | — |
| 14 | 130.1 | Q | — | — |
| 15 | 117.8 | CH | 6.52 | dd-1.9/7.9 Hz |
| 16 | 114.9 | CH | 6.67 | d-8.1 Hz |
| 17-18 | 144.7-144.6 | Q | — | — |
| 19 | 114.7 | CH | 6.81 | d-2.0 Hz |
| 20-21 | — | OH | 8.72-8.82 | s |
| 22 | — | OH | 9.03 | s |
| 23 | — | OH | 9.13 | s |
| 24 | — | OH | 5.05 | d-5.0 Hz |
| 14' | 15.2 | CH | 2.24 | sl |

The positions of the aromatic groups are moreover confirmed by $^{13}$C-$^{1}$H HMBC heteronuclear two-dimensional NMR.

EXAMPLE 9

Stability Under Basic Conditions of Derivatives Obtained by Thiolysis or by Sylvanolysis A buffer solution at pH 9 is prepared by adding 50 ml of a solution containing 0.2 mol/l of KCl and 0.2 mol/l of H$_3$BO$_3$ to 21.4 ml of a solution of NaOH at 0.2 mol/l.

Thiolysis

An aqueous solution containing 2 g/l of a crude product resulting from the depolymerization of a white seed tannin extract by thiolysis according to the protocol of Roumeas et al., 2013 is prepared. This solution contains the catechin (Cat) and epicatechin (Ec) terminal units, and also the sulfur-containing extension units derived from catechin (Cat-M) and from epicatechin (Ec-M). The UPLC chromatogram at 280 nm of this solution is shown in FIG. 6(a).

500 μl of this solution are transferred into a vial to which are added 500 μl of the buffer solution at pH 9. The vial is flushed with argon, sealed and left in the dark for 19 h. The UPLC chromatogram at 280 nm, of the resulting solution, is shown in FIG. 6(b). The disappearance of the peaks corresponding to the sulfur-containing extension units is observed therein. An analysis by UPLC-MS(+) shows that these sulfur-containing extension units have been more than 95% degraded in 19 h.

Sylvanolysis

In a first experiment, an aqueous solution containing 2 g/l of a crude product resulting from the depolymerization of a white seed tannin extract with the sylvan according to the protocol described in example 8 is prepared. This solution contains the catechin (Cat), epicatechin (Ec) and epicatechin gallate (EcG) terminal units, and also the sylvanylated extension units (2-methylfurylated) derived from catechin (Cat-S), from epicatechin (Ec-S) and from epicatechin gallate (EcG-S). The UPLC chromatogram at 280 nm of this solution is shown in FIG. 7(a).

500 µl of this solution are transferred into a vial to which are added 500 µl of the buffer solution. The vial is flushed with argon, sealed and left in the dark for 19 h. The UPLC chromatogram at 280 nm, of the resulting solution, is shown in FIG. 7(b). It is observed therein that the peaks corresponding to the sylvanylated extension units are always present. An analysis by UPLC-MS(+) shows that there was no degradation of the product after 19 h.

In a second experiment, the same product resulting from depolymerization of white seed tannins by sylvanolysis is dissolved at a concentration of 1 g/l in a solution of acetonitrile containing triethylamine at two concentrations, 0.02 or 1.8 mM (at these concentrations, the triethylamine in aqueous phase would form solutions at pH 10 and at pH 11, respectively). The two solutions are left under argon for 4 days in the dark in sealed vials. The analysis thereof by UPLC-MS(+) shows no degradation after 4 days.

EXAMPLE 10

Determination of the "Nucleophile/Depolymerizable Condensed Tannins" Molar Ratios for Furan and Sylvan A test carried out using a model tannin, the dimer B2, and either sylvan or furan as nucleophile, was developed in order to determine the minimum "nucleophile/depolymerizable condensed tannins" molar ratios to be used in the condensed tannin depolymerization reactions. In order to obtain a discriminating result, the test is based on the measurement of the rate of conversion with respect to units of derivatives of interest (furylated derivative or sylvanylated derivative) over a short reaction time, that is to say 10 min. Consequently, the rat measured in this test on initial reaction rates does not correspond to the degree of conversion obtained at the end of the reaction owing to the reaction kinetics. However, the comparison of the results of the test on the dimer B2 with those of the experiments which were carried out under real conditions on the industrial extract of white seed tannins for a maximum period of 8 h while retaining the same conditions of temperature, acidity and "nucleophile/tannins expressed in monomer equivalent" molar ratio outside this test and the results of which are presented in tables 2 and 4 of this document, makes it possible to establish a correlation between the degree of conversion in the test and the yields of production of the compounds of interest obtained under real conditions. Thus, a threshold lying at around 2.5% for the degree of conversion in the context of the test makes it possible to obtain, under the real production conditions, yields of compounds of interest of about 40%.

The curve which is determined by the test presented below then makes it possible to determine the minimum values of the "nucleophile/dimer B2 in monomer equivalent" molar ratios which correspond to the minimum "nucleophile/depolymerizable tannins in monomer equivalent" molar ratios that will have to be used in the depolymerization reactions under real conditions.

Described below is the procedure used to determine the "nucleophile/depolymerizable condensed tannins" molar ratio using a given tannin extract, taking furan or sylvan as nucleophile.

For an extract of given tannins, the molar amount of depolymerizable condensed tannins is determined by analytical thiolysis reaction, carried out in particular as described in the publication by Roumeas et al., 2013, and quantification of the amount of tannins thus depolymerized, by UPLC-MS, as indicated above.

The corresponding molar amount of nucleophile of general formula (III) is determined in the following way, for furan and sylvan.

A stock solution of dimer B2 is prepared at 100, 200 or 400 mg.l$^{-1}$ in MeOH (reference concentration: 400 mg.l$^{-1}$, that is to say 0.7 mM). The depolymerization solutions contain 200 mM of HCl and various concentrations of nucleophile of between 0.7 and 70 mM for sylvan, and 140 and 7000 mM for furan.

For each experiment, a mixture of 500 µl of stock solution of dimer B2 and 500 µl of depolymerization solution is prepared in a stoppered tube and immediately brought to 30° C. for 10 min. The samples are then directly analyzed by UPLC, according to the protocol described above, with neither treatment nor dilution beforehand. The quantification of the extension units $U_{ext}$ (in derivative form) and of terminal units $U_{term}$ released during the reaction makes it possible to calculate, for each test, the $U_{ext}/(U_{ext}+U_{term})$ ratio.

The results obtained, for each of furan and sylvan, as a function of the various "nucleophile/dimer B2 in monomer equivalents" molar ratios, are indicated in table 7 below.

TABLE 7

$U_{ext}/(U_{ext} + U_{term})$ molar ratios obtained by depolymerization of dimer B2 with furan and sylvan in accordance with the present invention

| "Nucleophile/dimer B2" molar ratio | Sylvan $U_{ext}/(U_{ext} + U_{term})$ molar ratio | Furan $U_{ext}/(U_{ext} + U_{term})$ molar ratio |
|---|---|---|
| 0.5 | 0.033* | — |
| 2.5 | 0.089* | — |
| 0.5 | 0.014** | — |
| 0.5 | 0.020* | — |
| 5 | 0.167* | — |
| 5 | 0.080*** | — |
| 5 | 0.140* | — |
| 10 | 0.170* | — |
| 50 | 0.420*** | — |
| 50 | 0.320* | — |
| 100 | — | 0.035* |
| 250 | — | 0.070* |
| 500 | 0.470** | 0.135* |
| 500 | 0.500* | — |
| 500 | 0.500*** | — |
| 3750 | — | 0.430*** |
| 5000 | — | 0.420* | with:
*experiments carried out in the presence of 0.35 mM of dimer B2
**experiments carried out in the presence of 0.087 mM of dimer B2
***experiments carried out in the presence of 0.17 mM of dimer B2

On the basis of these results, the curves representing the $U_{ext}/(U_{ext}+U_{term})$ molar ratio as a function of the "nucleophile/dimer B2" molar ratios are plotted. The curves obtained, for furan and sylvan, are shown in FIG. 8.

The results obtained demonstrate the competition reactions which take place between the nucleophiles and the flavonoid compounds present in the medium. They thus allow a comparison of the power of the nucleophiles with one another. Thus, the figure clearly shows that sylvan is a better nucleophile than furan, in so far as similar degrees of conversion with respect to extension units ($U_{ext}/(U_{ext}+U_{term})$ molar ratio) are achieved for "nucleophile/dimer B2" molar ratios that are much lower in the case of sylvan.

For example, using as a basis the smoothing curves obtained from the experimental points, shown in FIG. 8, the "nucleophile/dimer B2" molar ratio required to achieve, under the conditions of the test, a degree of conversion of 2.5% with respect to extension units, relative to the total of the extension units and of the terminal units, can be established at 0.79 for sylvan, and at 63 for furan. The "nucleophile/dimer B2" molar ratio required to achieve, under the conditions of the test, a degree of conversion of 5% with respect to extension units, relative to the total of the extension units and of the terminal units, can be established at 1.67 for sylvan, and at 133 for furan.

The same experiment can be carried out, under similar conditions, for any other nucleophile of general formula (III) according to the invention.

EXAMPLE 11

Depolymerization of Tannins Directly from Douglas Pine Bark

Comparative Example—Thiolysis

A thiolysis reaction, according to the protocol described in the publication by Roumeas et al., 2013, is carried out in the following way.

In a 100 ml round-bottomed flask, the Douglas pine bark (800 mg) is suspended in 40 ml of mercaptolysis solution (2.0 ml of 2-mercaptoethanol and 333 µl of fuming HCl per 40 ml of MeOH qs), and left to stir for 2 h at 40° C. The results obtained by UPLC-MS show a maximum content of extension unit of 129 µmol.g$^{-1}$ of initial bark.

Depolymerization Process with Sylvan in Accordance with the Invention

In a round-bottomed flask, the Douglas pine bark milled to 6 mm (10.0 g) is suspended in MeOH (75 ml), then sylvan (25 ml) and then fuming HCl (833 µl) are added with stirring. The mixture is brought to 30° C., and the reaction is monitored by UPLC-MS. After 2 h 30, the sylvanylated derivative yield reaches a maximum of 119 µmol.g$^{-1}$ of bark, that is to say 92% of the value obtained by means of the comparative thiolysis reaction.

The targeted sylvanylated derivatives are thus obtained with a high yield, directly from the bark, without prior tannin extraction.

Preparative Extraction

The reaction mixture obtained by means of the sylvanolysis reaction is filtered through a Büchner funnel in order to remove the bark, and 100 ml of an aqueous solution of NaHCO$_3$ (8.4 g.l$^{-1}$) are added. The solution obtained is evaporated under vacuum in order to remove the methanol and the sylvan, and the aqueous suspension is extracted with AcOEt (3×100 ml). The organic phase is dried over Na$_2$SO$_4$ and evaporated under vacuum to give an oily orangey solid (1.25 g). This product is triturated from petroleum ether (3×50 ml) in order to remove the lipids and the terpenes, and then taken up in Et$_2$O (140 ml). The suspension is washed with brine (2×50 ml), then dried over Na$_2$SO$_4$ and evaporated under vacuum to give an orangey solid (920 mg) comprising 291 mg of sylvanylated derivatives.

LITERATURE REFERENCES

Adams et al., 1921. Furfural. Org. Synth. 1, 49
Burnett et al., 1948. Production of 2-Methylfuran by Vapor-Phase Hydrogenation of Furfural. Ind. Eng. Chem. 40, 502-505
Chen et al., 2009. One-pot depolymerizative extraction of proanthocyanidins from mangosteen pericarps. Food Chem. 114, 874-880
Li et al., 2012. Aqueous electrocatalytic hydrogenation of furfural using a sacrificial anode. Electrochimica Acta 64, 87-93
Liengprayoon et al., 2011. Glycolipid composition of *Hevea brasiliensis* latex. *Phytochemistry* 72, 1902-1913
Maréchal, 2001. Analyse des principaux facteurs impliqués dans le fractionnement combiné de pailles et de sons de blé en extrudeur bi-vis: obtention d'agro-matériaux [Analysis of the principal factors involved in the combined fractionation of wheat bran and straw in a twin-screw extruder: obtaining agro-materials]. Thesis defended on Sep. 10,2001. Laboratoire de Chimie Agro-Industrielle [Laboratory of Agro-Industrial Chemistry], UMR INRA/INP-Ensiacet. Toulouse
Prieur et al., 1994. Oligomeric and polymeric procyanidins from grape seeds. Phytochemistry 36, 781-784.
Rigaud et al., 1993. Normal-phase high-performance liquid chromatographic separation of procyanidins from cacao beans and grape seeds. J. Chromatogr. A 654, 255-260.
Roumeas et al., 2013. Depolymerization of condensed tannins in ethanol as a gateway to biosourced phenolic synthons. Green Chem. 15, 3268-3275
Selga et al., 2004. Efficient One Pot Extraction and Depolymerization of Grape (Vitis vinifera) Pomace Procyanidins for the Preparation of Antioxidant Thio-Conjugates. J. Agric. Food Chem. 52,467-473

The invention claimed is:
1. A compound of general formula (I):

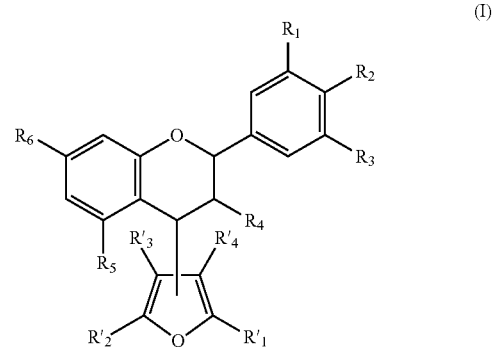

or a salt thereof, in which:
$R_1$, $R_2$, $R_3$ and $R_5$, which may be identical or different, each represent a hydrogen atom or a hydroxyl group, optionally protected by a hydroxyl-function-protecting group,
$R_4$ represents a hydrogen atom or an —OR$_7$ group, in which R$_7$ represents a hydrogen atom, a hydroxyl-function-protecting group, or a group of general formula (II):

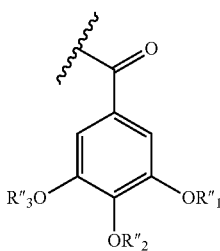

(II)

in which R"$_1$, R"$_2$ and R"$_3$, which may be identical or different, each represent a hydrogen atom or a hydroxyl-function-protecting group, R$_6$ represents a hydroxyl group, optionally protected by a hydroxyl-function-protecting group, and R'$_1$, R'$_2$, R'$_3$ and R'$_4$, which may be identical or different, each represent a hydrogen atom or a substituent which does not comprise:

any mesomeric-effect electron-withdrawing group which is conjugated to the furan nucleus, where one of R'$_1$, R'$_2$, R'$_3$ and R'$_4$ is a covalent bond with the pyran ring.

2. The compound as claimed in claim 1, in which R'$_1$, R'$_2$, R'$_3$ and R'$_4$, which may be identical or different, each representing, with the exception of said covalent bond with the pyran ring:

a hydrogen atom, a group comprising an electron-donating radical, said electron-donating radical being bonded directly or by conjugation to the furan ring and being optionally substituted, or a linear, branched or cyclic carbon-based radical, comprising a single ring or several condensed rings, which is saturated or unsaturated, optionally aromatic, which is optionally substituted, optionally comprising one or more heteroatoms or one or more groups comprising one or more heteroatoms.

3. The compound as claimed in claim 1, in which at least one substituent among R'$_1$, R'$_2$, R'$_3$ and R'$_4$ represents a hydrogen atom.

4. The compound as claimed in claim 1, in which R'$_1$ is said covalent bond with the pyran ring.

5. The compound as claimed in claim 1, in which R'$_3$ and R'$_4$ each represent a hydrogen atom.

6. The compound as claimed in claim 1, in which R'$_2$ represents a hydrogen atom or a C$_1$-C$_{18}$ alkyl group.

7. A method for obtaining a compound as claimed in claim 1, comprising a depolymerization step of depolymerizing condensed tannins in the presence of an acid by means of a nucleophile of general formula (III):

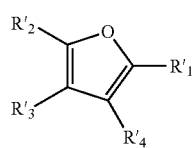

(III)

in which R'$_1$, R'$_2$, R'$_3$ and R'$_4$, which may be identical or different, each represent a hydrogen atom or a substituent which does not comprise:

any mesomeric-effect electron-withdrawing group which is conjugated to the furan nucleus, at least one substituent among R'$_1$, R'$_2$, R'$_3$ and R'$_4$ representing a hydrogen atom.

8. The method as claimed in claim 7, wherein, for the depolymerization step, the molar ratio of said "nucleophile of general formula (III): depolymerizable condensed tannins" is greater than or equal to the molar ratio of said "nucleophile of general formula (III): 2R,2'R,3R,3'R,4R)-2,2'-Bis(3,4-dihydroxyphenyl)-3,3',4,4'-tetrahydro-2H,2'H-4,8'-bichromene-3,3',5,5',7,7'-hexol" required to obtain at least a 2.5% yield of compounds of general formula (I), relative to a total of depolymerized compounds formed during a reaction of depolymerization of (2R,2'R,3R,3'R,4R)-2,2'-Bis(3,4-dihydroxyphenyl) -3,3',4,4'-tetrahydro-2H,2'H-4, 8'-bichromene-3,3',5,5',7,7'-hexol by said nucleophile of general formula (III) in a presence of hydrochloric acid at 0.1 N in methanol, at 30° C. and in a reaction time of 10 minutes.

9. The method as claimed in claim 7, wherein R'$_1$, R'$_2$, R'$_3$ and R'$_4$, which may be identical or different, each represent:

a hydrogen atom, a group comprising an electron-donating radical, said electron-donating radical being bonded directly or by conjugation to the furan ring and being optionally substituted, or a linear, branched or cyclic carbon-based radical, comprising a single ring or several condensed rings, which is saturated or unsaturated, optionally aromatic, which is optionally substituted, optionally comprising one or more heteroatoms or one or more groups comprising one or more heteroatoms.

10. The method as claimed in claim 7, wherein, in general formula (III), at least R'$_1$ represents a hydrogen atom.

11. The method as claimed in claim 7, wherein, in general formula (III), at least R'$_3$ and R'$_4$ each represent a hydrogen atom.

12. The method as claimed in claim 7, in which R'$_2$ represents a hydrogen atom or a C$_1$-C$_{18}$ alkyl group.

13. The method as claimed in claim 7, wherein for the depolymerization step, the acid is used in a concentration which is equivalent to the concentration of said acid that is required to confer a pH of between −1 and 3.5 on an aqueous solution.

14. The method as claimed in claim 7, wherein the depolymerization step is carried out in a polar solvent or in a mixture of solvents containing at least one polar solvent.

15. The method as claimed in claim 7, wherein the depolymerization step is carried out at a temperature below or equal to a boiling point of the nucleophile of general formula (III) at an applied pressure, and at less than or equal to a boiling point of the solvent at said applied pressure.

16. The method as claimed in claim 7, comprising a prior step of extracting the condensed tannins from biomass.

17. The method as claimed in claim 7, wherein the depolymerization step is carried out directly from biomass.

18. A method for depolymerizing condensed tannins, comprising a step of using a compound of general formula (III) to depolymerize the condensed tannins:

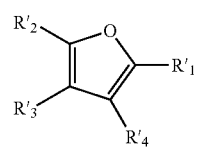

(III)

wherein $R'_1$, $R'_2$, $R'_3$ and $R'_4$, which may be identical or different, each represent a hydrogen atom or a substituent which does not comprise any mesomeric-effect electron-withdrawing group which is conjugated to the furan nucleus, and wherein at least one of $R'_1$, $R'_2$, $R'_3$ and $R'_4$ represents a hydrogen atom.

19. The method of claim 18, wherein $R'_1$ represents a hydrogen atom.

20. The method of claim 18, wherein $R'_3$ and $R'_4$ each represent a hydrogen atom.

21. The method of claim 18, wherein $R'_2$ represents a hydrogen atom or a $C_1$-$C_{18}$ alkyl group.

* * * * *